(12) United States Patent
Gu et al.

(10) Patent No.: US 12,161,720 B2
(45) Date of Patent: Dec. 10, 2024

(54) CELL ASSEMBLY-MEDIATED DELIVERY OF CHECKPOINT INHIBITORS FOR CANCER IMMUNOTHERAPY

(71) Applicant: NORTH CAROLINA STATE UNIVERSITY, Raleigh, NC (US)

(72) Inventors: Zhen Gu, Los Angeles, CA (US); Quanyin Hu, Jamaica Plain, MA (US)

(73) Assignee: North Carolina State University, Raleigh, NC (US)

(*) Notice: Subject to any disclaimer, the term of this patent is extended or adjusted under 35 U.S.C. 154(b) by 1029 days.

(21) Appl. No.: 17/045,586

(22) PCT Filed: Apr. 8, 2019

(86) PCT No.: PCT/US2019/026258
§ 371 (c)(1),
(2) Date: Oct. 6, 2020

(87) PCT Pub. No.: WO2019/195819
PCT Pub. Date: Oct. 10, 2019

(65) Prior Publication Data
US 2021/0023219 A1    Jan. 28, 2021

Related U.S. Application Data

(60) Provisional application No. 62/653,843, filed on Apr. 6, 2018.

(51) Int. Cl.
*A61K 45/06* (2006.01)
*A61K 47/69* (2017.01)
*C07K 16/28* (2006.01)

(52) U.S. Cl.
CPC .......... *A61K 45/06* (2013.01); *A61K 47/6929* (2017.08); *C07K 16/2818* (2013.01); *C07K 16/2827* (2013.01)

(58) Field of Classification Search
CPC .... A61K 39/395; A61K 39/505; A61K 35/19; A61K 2039/505; A61K 47/6929; A61K 47/6931; A61K 47/6927
See application file for complete search history.

(56) References Cited

U.S. PATENT DOCUMENTS

| | | |
|---|---|---|
| 3,610,795 A | 10/1971 | Antoine |
| 2012/0028350 A1 | 2/2012 | Dennis et al. |
| 2016/0354313 A1 | 12/2016 | De Beer |
| 2016/0367481 A1 | 12/2016 | Zale et al. |
| 2017/0000894 A1 | 1/2017 | Won et al. |
| 2017/0008858 A1 | 1/2017 | Van Delft et al. |
| 2018/0133342 A1* | 5/2018 | Yoo ............... A61K 51/0478 |
| 2018/0214487 A1 | 8/2018 | Fiorina |

FOREIGN PATENT DOCUMENTS

| | | | |
|---|---|---|---|
| CN | 107496937 A | * 12/2017 | ........... A61K 31/555 |
| JP | H08109142 A | 4/1996 | |
| JP | 2004231575 A | 8/2004 | |
| JP | 2010540535 A | 12/2010 | |
| WO | 2015/051465 A1 | 4/2015 | |
| WO | 2016205144 A1 | 12/2016 | |
| WO | 2017015320 A1 | 1/2017 | |
| WO | 2018/053010 A1 | 3/2018 | |

OTHER PUBLICATIONS

Xu et al., Nature:Scientific Reports, 2016, 1-16.*
Lallana et al., Pharm Res, 29, 2012, 1-34.*
Koo et al., Angewandte Chem Int Ed, 51, 2012, 11836-11840.*
International Search Report and Written Opinion issued in PCT/US2019/026258, dated Jun. 17, 2019, 12 pages.
Zeng et al. "Comparison of Conjugation Strategies of Cross-Bridged Macrocyclic Chelators with Cetuximab for Copper-64 Radiolabeling and PET Imaging of EGFR in Colorectal Tumor-Bearing Mice," Molecular Pharmaceutics, Apr. 10, 2014 (Apr. 10, 2014), vol. 11, No. 11, pp. 3980-3987.
Abbina et al. "Surface Engineering for Cell-Based Therapies: Techniques for Manipulating Mammalian Cell Surfaces," ACS Biomaterials Science & Engineering, Sep. 11, 2017 (Sep. 11, 2017), vol. 4, pp. 3658-3677.
Office Action issued on Feb. 28, 2023 in corresponding Japanese Application No. 2020-554396, 6 pages.
Extended European Search Report, dated Feb. 14, 2022, received in connection with corresponding EP Patent Application No. 19781585.5.
Senter, et al., *Bioconjugate Chem.*, 2:447-451, (1991).
Bagshawe, K.D., *Br. J. Cancer*, 60:275-281, (1989).
Bagshawe, et al., *Br. J. Cancer*, 58:700-703, (1988).
Senter, et al., *Bioconjugate Chem.*, 4:3-9, (1993).
Battelli, et al., *Cancer Immunol. Immunother.*, 35:421-425, (1992).
Pietersz and McKenzie, *Immunolog. Reviews*, 129:57-80, (1992).
Roffler, et al., *Biochem. Pharmacol*, 42:2062-2065, (1991).
Hughes et al., *Cancer Research*, 49:6214-6220, (1989).
Litzinger and Huang, *Biochimica et Biophysica Acta*, 1104:179-187, (1992).
Brown and Greene, *DNA and Cell Biology* 10:6, 399-409 (1991).
*Handbook of Monoclonal Antibodies*, Ferrone et al., eds., Noges Publications, Park Ridge, N.J., (1985) ch. 22 and pp. 303-357.
Smith et al., *Antibodies in Human Diagnosis and Therapy*, Haber et al., eds., Raven Press, New York (1977) pp. 365-389.
Advani, R. et al. Treatment of refractory and relapsed acute myelogenous leukemia with combination chemotherapy plus the multidrug resistance modulator PSC 833 (Valspodar). *Blood* 93, 787-795 (1999).
Brentjens, R. J. et al. CD19-targeted T cells rapidly induce molecular remissions in adults with chemotherapy-refractory acute lymphoblastic leukemia. *Sci. Transl. Med.* 5, 177ra138-177ra138 (2013).

(Continued)

*Primary Examiner* — Kyle A Purdy
(74) *Attorney, Agent, or Firm* — Meunier Carlin & Curfman LLC

(57) ABSTRACT

Disclosed are therapeutic agent delivery vehicle comprising a modified platelet comprising a therapeutic agent cargo and a targeting moiety and methods for treating cancer comprising administering the same to a subject.

15 Claims, 7 Drawing Sheets

(56) References Cited

OTHER PUBLICATIONS

Figure 1:
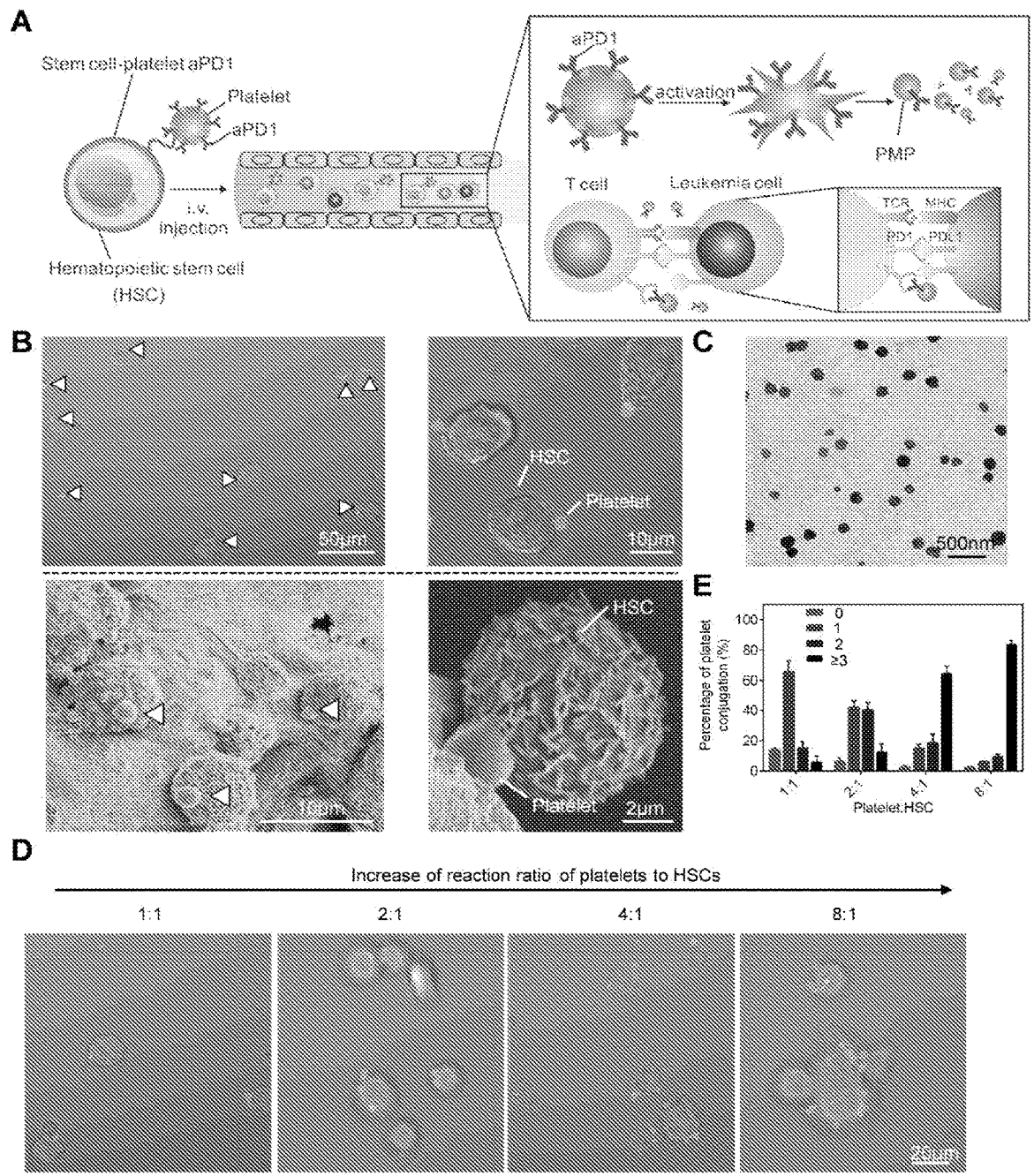

Costinean, S. et al. Pre-B cell proliferation and lymphoblastic leukemia/high-grade lymphoma in Eµ-miR155 transgenic mice. *Proc. Natl Acad. Sci. USA* 103, 7024-7029 (2006).
Dick, J. E. Acute myeloid leukemia stem cells. *Ann. N. Y. Acad. Sci.* 1044, 1-5 (2005).
Ding, L. et al. Clonal evolution in relapsed acute myeloid leukemia revealed by whole genome sequencing. *Nature* 481, 506 (2012).
Döhner, H. et al. Diagnosis and management of acute myeloid leukemia in adults: recommendations from an international expert panel, on behalf of the European LeukemiaNet. *Blood* 115, 453-474 (2010).
Eeftens, J. M., van der Torre, J., Burnham, D. R. & Dekker, C. Copper-free click chemistry for attachment of biomolecules in magnetic tweezers. *BMC biophysics* 8, 9 (2015).
Ellebrecht, C. T. et al. Reengineering chimeric antigen receptor T cells for targeted therapy of autoimmune disease. *Science* 353, 179-184 (2016).
Estey, E. & Dohner, H. Acute myeloid leukaemia. *The Lancet* 368, 1894-1907 (2006).
Fernandez, H. F. et al. Anthracycline dose intensification in acute myeloid leukemia. *N. Engl. J. Med.* 361, 1249-1259 (2009).
Giralt, S. A. & Champlin, R. E. Leukemia relapse after allogeneic bone marrow transplantation: a review. *Blood* 84, 3603-3612 (1994).
Gottesman, M. M., Fojo, T. & Bates, S. E. Multidrug resistance in cancer: role of ATP-dependent transporters. *Nat. Rev. Cancer* 2, 48 (2002).
Hang, H. C., Yu, C., Kato, D. L. & Bertozzi, C. R. A metabolic labeling approach toward proteomic analysis of mucin-type O-linked glycosylation. *Proc. Natl Acad. Sci. USA* 100, 14846-14851 (2003).
Hu, C.-M. J. et al. Nanoparticle biointerfacing by platelet membrane cloaking. *Nature* 526, 118-121 (2015).
Hu, Q. et al. Engineered nanoplatelets for enhanced treatment of multiple myeloma and thrombus. *Adv. Mater.* 28, 9573-9580 (2016).
Huntly, B. J. & Gilliland, D. G. Leukaemia stem cells and the evolution of cancer-stem-cell research. *Nat. Rev. Cancer* 5, 311-321 (2005).
Ishida, Y., Agata, Y., Shibahara, K. & Honjo, T. Induced expression of PD-1, a novel member of the immunoglobulin gene superfamily, upon programmed cell death. *The EMBO journal* 11, 3887 (1992).
Jackson, H. J., Rafiq, S. & Brentjens, R. J. Driving CAR T-cells forward. *Nat. Rev. Clin. Oncol.* 13, 370-383 (2016).
Kamath, S., Blann, A. & Lip, G. Platelet activation: assessment and quantification. *Eur. Heart J.* 22, 1561-1571 (2001).
Keir, M. E. et al. Tissue expression of PD-L1 mediates peripheral T cell tolerance. *J. Exp. Med.* 203, 883-895 (2006).
Kershaw, M. H., Westwood, J. A. & Darcy, P. K. Gene-engineered T cells for cancer therapy. *Nat. Rev. Cancer* 13, 525-541 (2013).
Kingwell, K. CAR T therapies drive into new terrain. *Nat. Rev. Drug Discovery* 16, 301-304 (2017).
Lagasse, E. et al. Purified hematopoietic stem cells can differentiate into hepatocytes in vivo. *Nat. Med.* 6, 1229 (2000).
Leith, C. P. et al. Acute myeloid leukemia in the elderly: assessment of multidrug resistance (MDR1) and cytogenetics distinguishes biologic subgroups with remarkably distinct responses to standard chemotherapy. A Southwest Oncology Group study. *Blood* 89, 3323-3329 (1997).
Leith, C. P. et al. Frequency and clinical significance of the expression of the multidrug resistance proteins MDR1/P-glycoprotein, MRP1, and LRP in acute myeloid leukemia. A Southwest Oncology Group Study. *Blood* 94, 1086-1099 (1999).
Leopold, L. H. & Willemze, R. The treatment of acute myeloid leukemia in first relapse: a comprehensive review of the literature. *Leuk. Lymphoma* 43, 1715-1727 (2002).
Lowenberg, B., Downing, J. R. & Burnett, A. Acute myeloid leukemia. *N. Engl. J. Med.* 1999, 1051-1062 (1999).
Maude, S. L. et al. Chimeric antigen receptor T cells for sustained remissions in leukemia. *N. Engl. J. Med.* 371, 1507-1517 (2014).
McClanahan, F. et al. PD-L1 checkpoint blockade prevents immune dysfunction and leukemia development in a mouse model of chronic lymphocytic leukemia. *Blood* 126, 203-211 (2015).
Miyazaki, Y. et al. High shear stress can initiate both platelet aggregation and shedding of procoagulant containing microparticles. *Blood* 88, 3456-3464 (1996).
Moynihan, K. D. et al. Eradication of large established tumors in mice by combination immunotherapy that engages innate and adaptive immune responses. *Nat. Med.* 22, 1402-1410 (2016).
Ofran, Y. & Rowe, J. M. Treatment for relapsed acute myeloid leukemia: what is new? *Curr. Opin. Hematol.* 19, 89-94 (2012).
Pandolfi, A. et al. PAK1 is a therapeutic target in acute myeloid leukemia and myelodysplastic syndrome. *Blood* 126, 1118-1127 (2015).
Ruggeri, Z. M., Orje, J. N., Habermann, R., Federici, A. B. & Reininger, A. J. Activation-independent platelet adhesion and aggregation under elevated shear stress. *Blood* 108, 1903-1910 (2006).
Shi, P. et al. Spatiotemporal control of cell-cell reversible interactions using molecular engineering. *Nat. Commun.* 7 (2016).
Swami, A. et al. Engineered nanomedicine for myeloma and bone microenvironment targeting. *Proc. Natl Acad. Sci. USA* 111, 10287-10292 (2014).
Topalian, S. L. et al. Safety, activity, and immune correlates of anti-PD-1 antibody in cancer. *N. Engl. J. Med.* 366, 2443-2454 (2012).
Topalian, S. L., Drake, C. G. & Pardoll, D. M. Immune checkpoint blockade: a common denominator approach to cancer therapy. *Cancer Cell* 27, 450-461 (2015).
Tumeh, P. C. et al. PD-1 blockade induces responses by inhibiting adaptive immune resistance. *Nature* 515, 568 (2014).
Velez, J. et al. Platelets promote mitochondrial uncoupling and resistance to apoptosis in leukemia cells: a novel paradigm for the bone marrow microenvironment. *Cancer Microenviron.* 7, 79-90 (2014).
Wang, C. et al. In situ activation of platelets with checkpoint inhibitors for post-surgical cancer immunotherapy. *Nature Biomedical Engineering* 1, 0011 (2017).
Wilson, A. & Trumpp, A. Bone-marrow haematopoietic-stem-cell niches. *Nat. Rev. Immunol.* 6, 93-106 (2006).
Wu, C.-Y., Roybal, K. T., Puchner, E. M., Onuffer, J. & Lim, W. A. Remote control of therapeutic T cells through a small molecule-gated chimeric receptor. *Science* 350, aab4077 (2015).
Yan, M. & Jurasz, P. The role of platelets in the tumor microenvironment: From solid tumors to leukemia. *Biochim. Biophys. Acta* 1863, 392-400 (2016).
Yuan, H. et al. Multivalent bi-specific nanobioconjugate engager for targeted cancer immunotherapy. *Nat. Nanotechnol.* 12, 763-769 (2017).
Zhang, L., Gajewski, T. F. & Kline, J. PD-1/PD-L1 interactions inhibit antitumor immune responses in a murine acute myeloid leukemia model. *Blood* 114, 1545-1552 (2009).
Zhao, M. et al. Clickable Protein Nanocapsules for Targeted Delivery of Recombinant p53 Protein. *J. Am. Chem. Soc.* 136, 15319-15325 (2014).
Zhou, Q. et al. Depletion of endogenous tumor-associated regulatory T cells improves the efficacy of adoptive cytotoxic T-cell immunotherapy in murine acute myeloid leukemia. *Blood* 114, 3793-3802 (2009).
Zhou, Q. et al. Program death-1 signaling and regulatory T cells collaborate to resist the function of adoptively transferred cytotoxic T lymphocytes in advanced acute myeloid leukemia. *Blood* 116, 2484-2493 (2010).
International Preliminary Report on Patentability issued for Application No. PCT/US2019/026258, dated Oct. 15, 2020.

\* cited by examiner

FIG. 1A, FIG. 1B, FIG. 1C, FIG. 1D, and FIG. 1E

FIG. 3A, FIG. 3B, and FIG. 3C
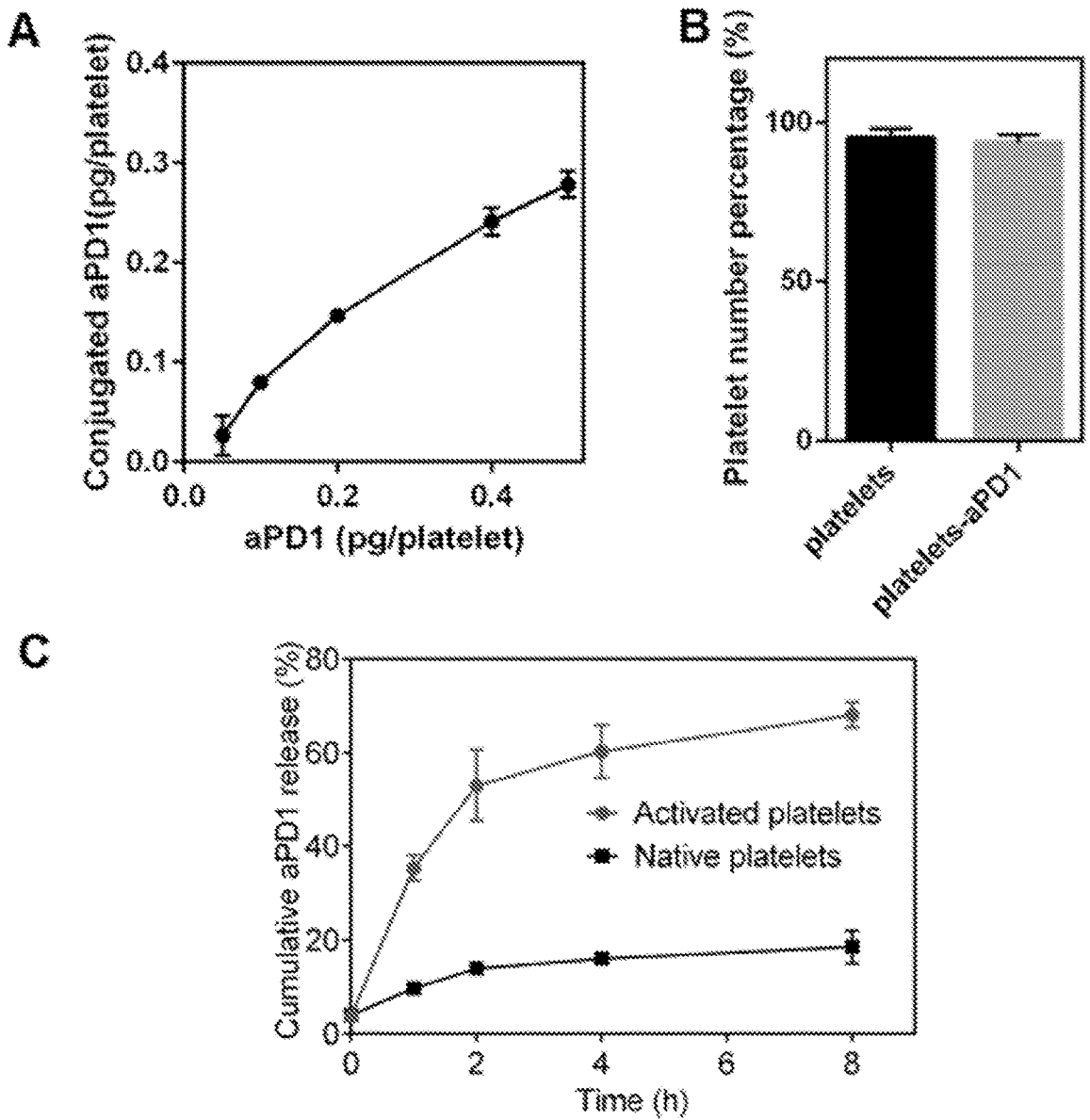

FIG. 4A, FIG. 4B, FIG. 4C, FIG. 4D, FIG. 4E, FIG. 4F, FIG. 4G, FIG. 4H, FIG. 4I, and FIG. 4J
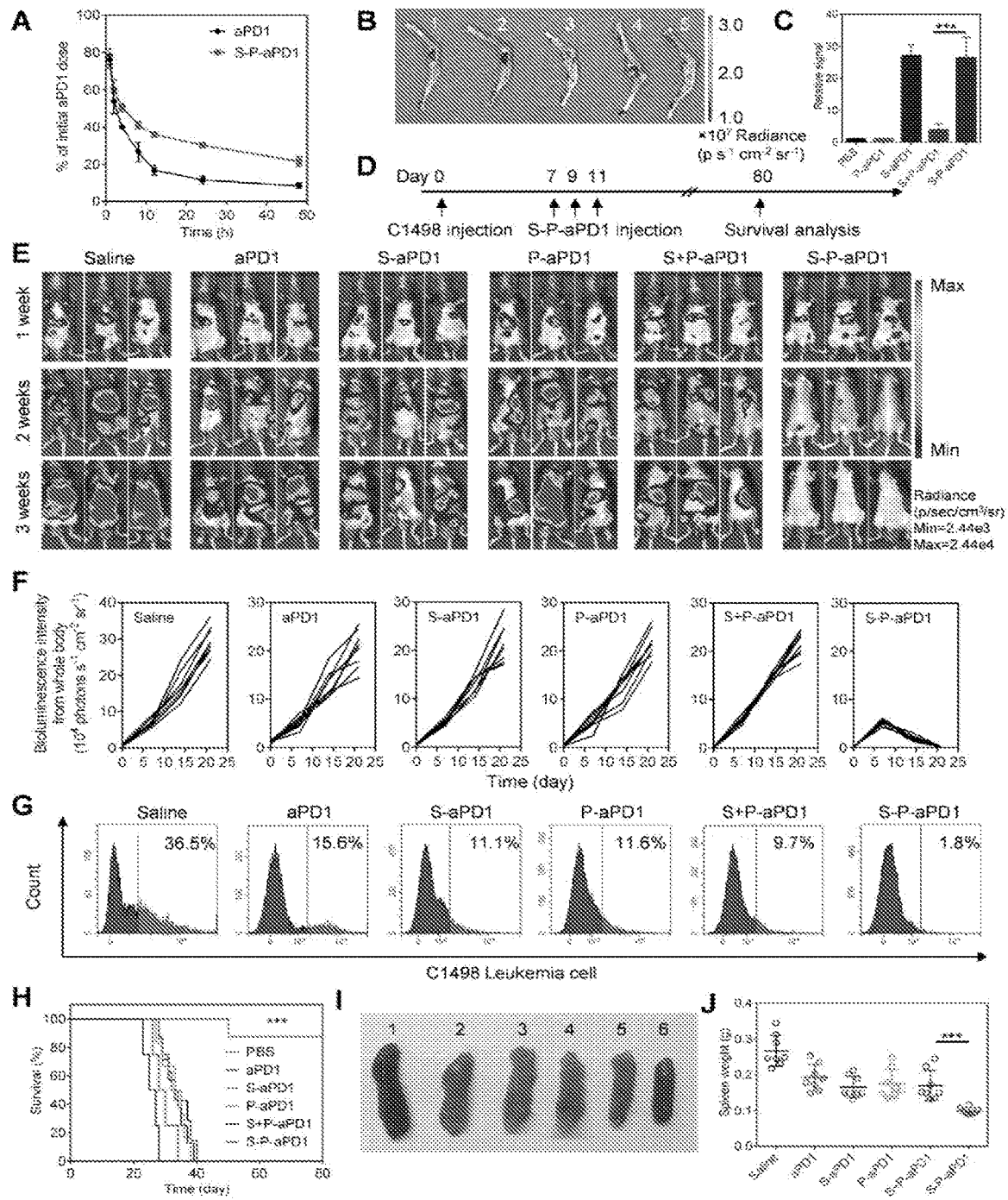

FIG. 5A, FIG. 5B, FIG. 5C, FIG. 5D, and FIG. 5E
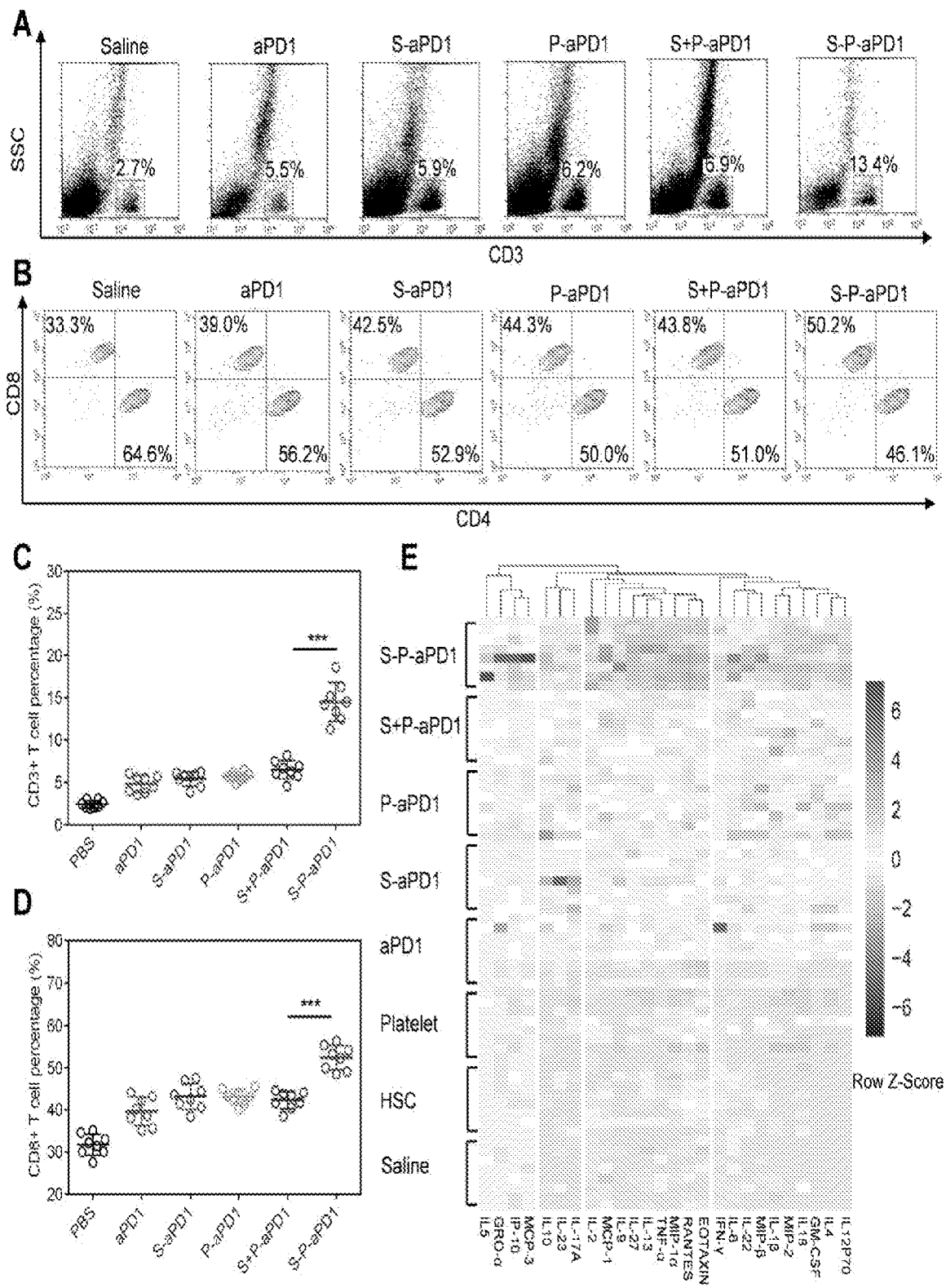

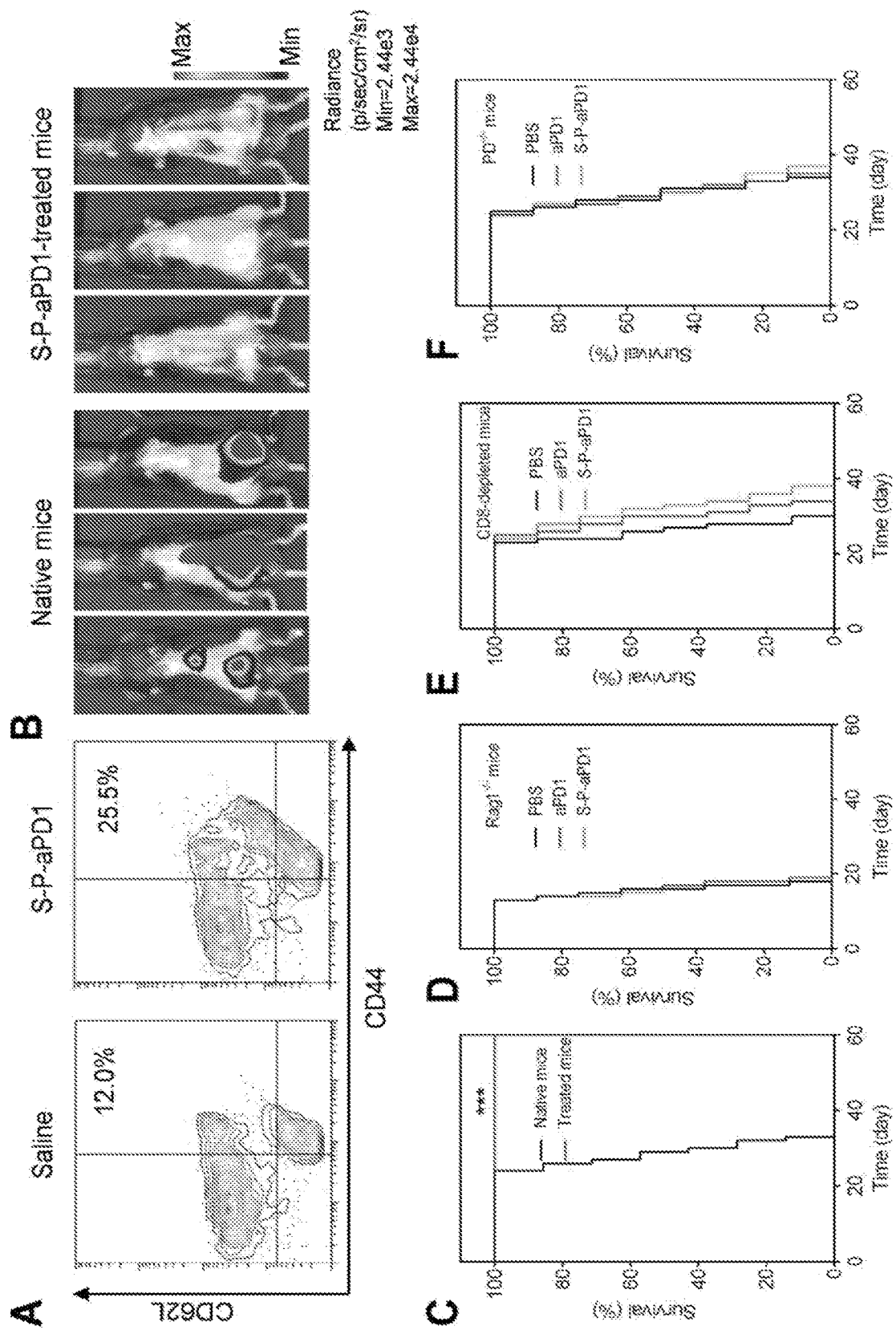
FIG. 7A, FIG. 7B, FIG. 7C, FIG. 7D, FIG. 7E, and FIG. 7F

CELL ASSEMBLY-MEDIATED DELIVERY OF CHECKPOINT INHIBITORS FOR CANCER IMMUNOTHERAPY

This is a national stage application filed under 35 U.S.C § 371 of PCT International Application No. PCT/US2019/026258, filed Apr. 8, 2019, entitled "CELL ASSEMBLY-MEDIATED DELIVERY OF CHECKPOINT INHIBITORS FOR CANCER IMMUNOTHERAPY," which claims the benefit of U.S. Provisional Application No. 62/653,843, filed on Apr. 6, 2019, applications which are incorporated herein by reference in their entireties.

I. BACKGROUND

The traditional treatment for acute myeloid leukemia (AML), a clonal malignancy comprising an increase in myeloblasts in the bone marrow, includes an anthracycline and cytarabine-based chemotherapy regimens. However, efficacy of traditional chemotherapy for AML is far from satisfactory, as the majority of patients who achieve a complete remission will ultimately relapse, due to the incomplete elimination of leukemia cells. The prognosis of patients with relapsed leukemia is dismal. Although relapsed leukemia could be potentially cured by hematopoietic stem cell transplantation, the cost of such transplantation is often associated with high mortality that is induced by infections or graft-versus-host disease. The emerging technologies of engineering T cells provide a potentially new approach to treat AML. T cells from patients themselves could be removed from the circulation and genetically modified to express an artificial T cell receptor (designated as chimeric antigen receptor) in vitro that is designed to specifically recognize the tumor-associated antigens. Chimeric antigen receptor-modified T cells (CAR-T) enable the redirection of T-cell specificity and achieve impressive treatment outcomes against blood cancers in the clinic. However, genetic engineering of T cells often involves complex and expensive ex vivo manipulation. In addition, alleviation of the side effects, such as cytokine storm and B cell aplasia, remains clinically challenging. Development of new treatment approaches that can effectively eliminate leukemia cells and avoid side effects is therefore highly desirable to enhance the therapeutic efficacy and prognosis of patients with AML.

II. SUMMARY

Disclosed are methods and compositions related to therapeutic agent delivery vehicles comprising a drug or drug carrier (such as for example, modified platelet) and a targeting moiety which can be used to deliver a therapeutic agent such as an antibody, small molecule, peptide, polypeptide, peptide mimetic, polymer, nucleic acid, or drug combination to a target site.

Accordingly, in one aspect, disclosed herein are therapeutic agent delivery vehicles comprising a drug or drug carrier (such as, for example, a modified platelet) and a targeting moiety; wherein the drug or drug carrier (such as, for example, a modified platelet) has been modified to comprise a therapeutic agent cargo and a chemical linkage; wherein the platelet is chemically conjugated to the targeting moiety.

In one aspect, disclosed herein are therapeutic agent delivery vehicles of any preceding aspect, wherein the drug or drug carrier can be either conjugated on the surface of targeting moiety or inside of targeting moiety. In one aspect, the drug or drug carrier includes the modified platelet, synthetic nanoparticle, synthetic microparticle and cell-derived vesicle. For example, in one aspect, the platelet has been modified to comprise a therapeutic agent cargo and a chemical linkage; wherein the platelet is chemically conjugated to the targeting moiety.

Also disclosed herein are therapeutic agent delivery vehicles of any preceding aspect, wherein the targeting moiety is a peptide, polypeptide, peptide mimetic, polymer, small molecule, nucleic acid, antibody, sugar, or cell. It is understood and herein contemplated that the targeting moiety can be designed or engineered to target the bone marrow, liver, spleen, pancreas, prostate, bladder, heart, lung, brain, skin, kidneys, ovaries, testis, lymph nodes, small intestines, large intestines, or stomach.

In one aspect, disclosed herein are therapeutic agent delivery vehicles of any preceding aspect, wherein the targeting moiety targets the bone marrow and the moiety is selected from the group consisting of hematopoietic stem cell, a peptide comprising repeats of Asp or Glu, or bone marrow targeting formulation.

Also disclosed herein are therapeutic agent delivery vehicles of any preceding aspect, wherein the platelet is chemically conjugated to the targeting moiety via copper(I) catalyzed [3+2] azide-alkyne cycloaddition (CuAAC), strain-promoted azide-alkyne cycloaddition (SPAAC), Strain-promoted alkyne-nitrone cycloaddition (SPANC), or Dibenzocyclooctyl (DBCO) Copper-Free cycloaddition (for example, a Dibenzocyclooctyl (DBCO)-polyethylene glycol (PEG) 4 NHS ester).

In one aspect, disclosed herein are therapeutic agent delivery vehicles of any preceding aspect, wherein the targeting moiety is treated with an activated azide molecule (such as, for example, N-azidoaceiyigalactosamine-tetraacylated (Ac4GalNAz)).

Also disclosed herein are therapeutic agent delivery vehicles of any preceding aspect, wherein the therapeutic agent cargo comprises an antibody, small molecule, peptide, polypeptide, peptide mimetic, polymer, or nucleic acid (for example, an immune checkpoint inhibitor such as for example, a PD-1 inhibitor, a PD-L1 inhibitor, or CTLA-4 inhibitor such as, for example, nivolumab, pembrolizumab, pidilizumab, BMS-936559, Atezolizumab, Durvalumab, or Avelumab).

In one aspect, disclosed herein are therapeutic agent delivery vehicles of any preceding aspect, wherein the immune checkpoint inhibitor is attached to the surface of the modified platelet via a sulfosuccinimidyl-4-(N-maleimidomethyl)-cyclohexane-1-carboxylate (Sulfo-SMCC) linker.

Also disclosed herein are methods of treating a cancer in a subject comprising administering to the subject the therapeutic agent delivery vehicle of any preceding aspect.

In one aspect, disclosed herein are methods of treating a cancer in a subject comprising administering to the subject a therapeutic agent delivery vehicle comprising a modified platelet and a targeting moiety; wherein the platelet has been modified to comprise a therapeutic agent cargo and a chemical linkage; wherein the chemical linkage comprises Dibenzocyclooctyl (DBCO)-polyethylene glycol (PEG) 4 NHS ester; and wherein the platelet is chemically conjugated to the targeting moiety.

Also disclosed herein are methods of treating a cancer of any preceding aspect, wherein the targeting moiety comprises a hematopoietic stem cell labeled with N-azidoacetyl-galactosamine-tetraacylated (Ac4GalNAz).

In one aspect, disclosed herein are methods of treating a cancer of any preceding aspect, wherein the therapeutic agent cargo comprises an antibody, small molecule, peptide, polypeptide, peptide mimetic, polymer, or nucleic acid (for example, an immune checkpoint inhibitor such as for example, a PD-1 inhibitor, a PD-L1 inhibitor, or CTLA-4 inhibitor such as, for example, nivolumab, pembrolizumab, pidilizumab, BMS-936559, Atezolizumab, Durvalumab, or Avelumab).

Also disclosed herein are methods of treating a cancer of any preceding aspect, wherein the cancer is selected from the group consisting of lymphoma, B cell lymphoma, T cell lymphoma, mycosis fungoides, Hodgkin's Disease, myeloid leukemia (including acute myeloid leukemia), bladder cancer, brain cancer, nervous system cancer, head and neck cancer, squamous cell carcinoma of head and neck, renal cancer, small cell lung cancer and non-small cell lung cancer, neuroblastoma, glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, genitourinary cancer, pulmonary cancer, esophageal carcinoma, head and neck carcinoma, large bowel cancer, hematopoietic cancers; testicular cancer; colon cancers, and rectal cancers.

Also disclosed herein are pharmaceutical compositions of any preceding aspect further comprising administering a chemotherapeutic agent such as, for example, a small molecule (including, but not limited to 1-methyl-tryptophan (1-MT), norharmane, rosmarinic acid, epacadostat, navooximod, doxombicin, tamoxifen, paclitaxel, vinblastine, cyclophosphamide, and 5-fluorouracil), siRNA, peptide, peptide mimetic, polymer, or antibody (such as, for example, and anti-PDL-1 antibody including, but not limited to Atexolizumab, Durvalumab, and Avelumab).

In one aspect, disclosed herein are methods of treating a cancer in a subject of any preceding aspect, wherein therapeutic agent delivery vehicles or pharmaceutical compositions are administered to the patient at least once every 12, 14, 16, 18, 20, 22, 24, 26, 28, 30, 32, 34, 36, 38, 40, 42, 44, 46, 48 hours, once every 3, 4, 5, 6, 7, 8, 9, 10, 11, 12, 13, 14, 15, 16, 17, 18, 19, 20, 21, 22, 23, 24, 25, 26, 27, 28, 29, 30, 31 days, once every 2, 3, 4, 5, 6, 7, 8, 9, 10, 11, or 12 months.

Also disclosed herein are methods of treating a cancer in a subject of any preceding aspect, wherein the therapeutic agent delivery vehicles or pharmaceutical compositions are administered at least 1, 2, 3, 4, 5, 6, 7 times per week.

In one aspect, disclosed herein are methods of treating a cancer in a subject of any preceding aspect, wherein the dose of the administered dose of the administered therapeutic agent delivery vehicle or pharmaceutical composition is from about 10 mg/kg to about 100 mg/kg.

Also disclosed herein are methods of treating a cancer in a subject of any preceding aspect, further comprising administering a chemotherapeutic agent.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, 1C, 1D, and 1E show the characterization of the S–P-aPD1 delivery system. FIG. 1A shows a schematic of HSC-Platelet assembly-assisted effective aPD1 delivery. After intravenous delivery, the S–P-aPD1 could home to the bone marrow and the platelets could be locally activated and release aPD1 to bind T cells for an enhanced immune response. PMP: platelet-derived microparticle. FIG. 1B shows confocal (upper) and SEM characterization (lower) of S–P-aPD1 conjugates. The platelets were labeled with rhodamine for confocal observation. White arrows indicate the presence of platelets. FIG. 1C shows TEM characterization of PMPs from S–P-aPD1 after activation by 0.5 U/mL thrombin. FIG. 1D shows fluorescence imaging of S–P-aPD1 in different ratios of platelets to HSCs. FIG. 1E shows the quantitative analysis of conjugated platelets on the HSCs. The quantification was based on counting S–P-aPD1 (numbers=200) under the confocal microscope. The experiments were repeated thrice (n=3).

Figure 2:
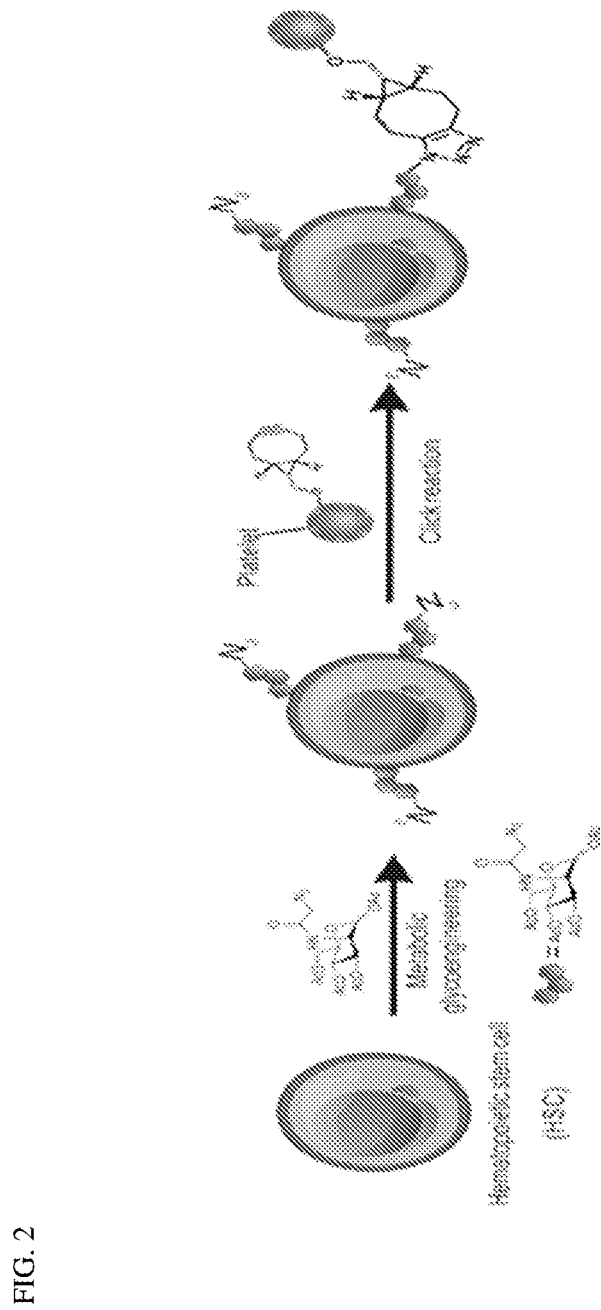

FIG. 2 shows a schematic of conjugation of platelets on HSC via click reaction.

FIGS. 3A, 3B, and 3C show the quantification of the conjugation amount of aPD1 on the platelets FIG. 3A shows the quantification of conjugated aPD1 on the surface of platelets. Error bars indicate s.d. (n=3). 0.2 pg aPD1/platelet was used in the following studies. FIG. 3B shows the integrity of native platelets and aPD1-conjugated platelets after 24 h of incubation. Error bars indicate s.d. (n=3). FIG. 3C shows in vitro cumulative aPD1 release from native platelets and activated platelets. Error bars indicate s.d. (n=3).

FIGS. 4A, 4B, 4C, 4D, 4E, 4F, 4G, 4H, 4I, and 4J show the In vivo treatment efficacy of S–P-aPD1. FIG. 4A shows in vivo pharmacokinetics of free aPD1 and S–P-aPD1 at the aPD1 dose of 1 mg/kg (n=3). FIG. 4B shows fluorescence images of bone tissues from the mice treated with Cy 5.5-labeled-free aPD1 (1), P-aPD1 (2), S-aPD1(3), S+P-aPD1 (4) and S–P-aPD1 (5). FIG. 4C shows region-of-interest analysis of fluorescent intensities from bone tissues. Error bars indicate s.d. (n=3). *$P<0.001$ (two-tailed Student's t-test). FIG. 4D shows a schematic representation of building C1498 leukemia model and treatment plan. FIG. 4E shows bioluminescence images of mice treated with PBS, free aPD1, S-aPD1, P-aPD1, S+P-aPD1 and S–P-aPD1 (HSCs/platelets: $5\times10^7$ cells in 100 μL PBS, aPD1: 0.5 mg/kg). FIG. 4F shows region-of-interest analysis of bioluminescence intensities from whole mice body. FIG. 4G shows flow cytometry analysis of the amount of C1498 cells in peripheral blood. FIG. 4H shows survival curves for treated and control mice (n=8). Statistical significance was calculated by log-rank test (*$P<0.001$). FIG. 4I shows the morphologies of spleens from the mice receiving different treatments (1: saline; 2: free aPD1; 3: S-aPD1; 4: P-aPD1; 5: S+P-aPD1; 6: S–P-aPD1). FIG. 4J shows the weights of the spleens. Error bars indicate s.d. (n=8). ***$P<0.001$ (two-tailed Student's t-test).

FIGS. 5A, 5B, 5C, 5D, and 5E show cytokines and chemokines and T cell analysis.

FIG. 5A shows flow cytometry analysis of CD3+ T cells in peripheral blood. FIG. 5B shows flow cytometry analysis of CD8+ T cells (gated on CD3+ T cells) in peripheral blood. FIG. 5C shows quantitative analysis of the amount of CD3+ T cells. Error bars indicate s.d. (n=8). *$P<0.001$ (two-tailed Student's t-test). FIG. 5D shows quantitative analysis of the amount of CD8+ T cells. Error bars indicate s.d. (n=8). *$P<0.001$ (two-tailed Student's t-test). FIG. 5E shows luminex-based quantification of cytokines and chemokines.

Figures 6A, 6B:
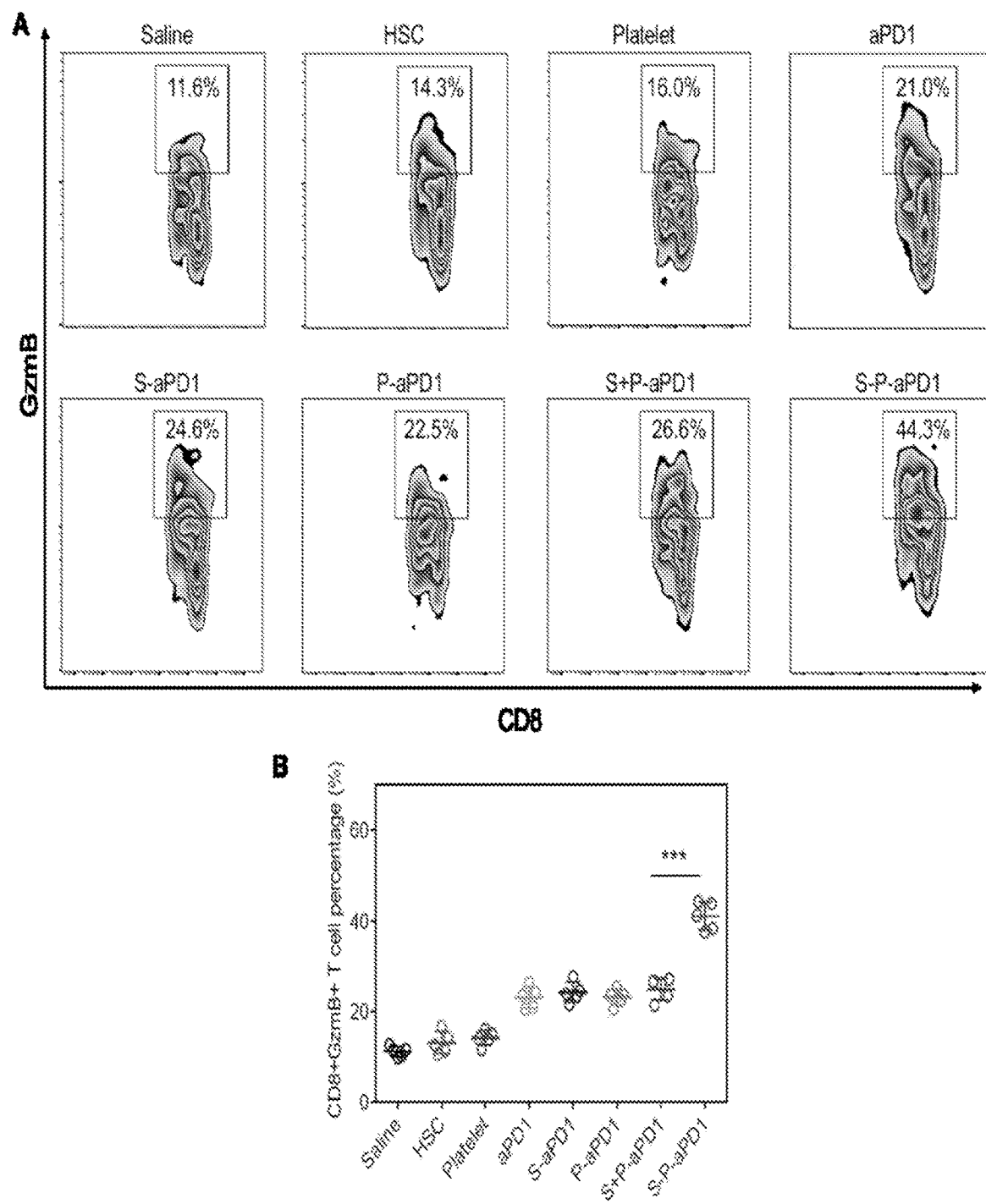

FIGS. 6A and 6B show analysis of Granzyme B+ (GzmB+) T cells. FIG. 6A shows flow cytometry analysis of CD8+GzmB+ T cells from the bone marrow of different treatment groups (n=5). FIG. 6B shows quantitative analysis of CD8+GzmB+ T cells in the bone marrow. Error bars indicate s.d. (n=5). ***$P<0.001$ (one-way ANOVA, followed by Tukey's HSD post hoc test).

FIGS. 7A, 7B, 7C, 7D, 7E, and 7F show that S-P-aPD1 induced a durable immune response. FIG. 7A shows flow cytometry analysis of $CD44^+CD62L^+$ T cells (gated on CD8+ T cells). FIG. 7B shows bioluminescence images of the native mice and treated mice re-challenged with $1\times10^6$ C1498 cells at 3 weeks. FIG. 7C shows survival curves for treated and native mice after C1498 cells re-challenge (n=8). Statistical significance was calculated by log-rank test (***P<0.001). FIG. 7D shows survival curves for $rag^{-/-}$ mice treated with PBS, free aPD1 and S-P-aPD1 at aPD1 dose of 0.5 mg/kg (n=8). FIG. 7E shows survival curves for CD8+ T cell depleted mice treated with PBS, free aPD1 and S-P-aPD1 at aPD1 dose of 0.5 mg/kg (n=8). FIG. 7F shows survival curves for $PD^{-/-}$ mice treated with PBS, free aPD1 and S-P-aPD1 at aPD1 dose of 0.5 mg/kg (n=8).

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood and herein contemplated that immunotherapy such as checkpoint inhibitor blockade can be effective in the treatment of cancers or relapse following surgical recision of a tumor. However, the antibodies used in these blockades result in limitations for many patients and are ineffective in many more. Programmed death-1 (PD-1) is an immune inhibitory co-receptor expressed on a variety of immune cells such as T cells, B cells and natural killer cells. When bound by its ligands, PD-L1/PD-L2, PD-1 functions by inhibiting an activated T cell response. Tumor cells up-regulate PD-L1 in response to inflammation thereby suppressing an anti-tumor immune response. Monoclonal antibody blockade of PD-1 (aPD1) inhibits tumor-mediated immune suppression and has been demonstrated to improve outcomes in a variety of cancers. Preclinical studies suggest that blocking the PD-1 pathway may improve outcomes in acute myeloid leukemia (AML). Thus, anti-PD-1 represents a promising strategy in the therapeutic armamentarium of AML. Herein is described an HSC-platelet assembly delivery system that can facilitate transport of aPD1 to the bone marrow and subsequent release of aPD1 by in situ platelet activation (FIG. 1A). The construction of HSC-platelet assembly is mediated by conjugation of platelet toward the HSC plasma membrane through a click reaction (FIG. 2) Immune checkpoint inhibitor aPD1 is covalently decorated on the surface of platelets. Furthermore, the release of aPD1 can be promoted through the generation of platelet-derived microparticles (PMPs) after activation of platelets, which further enhances the binding of aPD1 to T cells. After intravenous injection, it was demonstrated herein that HSC-platelet-aPD1 assembly (designated as S–P-aPD1) can effectively accumulate in the bone marrow, where the residual leukemia cells locate after traditional treatment. Using C1498 leukemia-bearing mice as AML model, it was found that S–P-aPD1 can completely eliminate the leukemia cells by inducing potent immune response through activation of T cells and generation of multiple cytokines and chemokines. Furthermore, such immune response is durable that can remarkably induce resistance to re-challenging leukemia cells. Accordingly, in one aspect, disclosed herein are therapeutic agent delivery vehicles comprising a modified platelet and a targeting moiety; wherein the platelet has been modified to comprise a therapeutic agent cargo and a chemical linkage; wherein the platelet is chemically conjugated to the targeting moiety.

It is understood and herein contemplate that the therapeutic agent delivery vehicles are designed to target the therapeutic agent cargo to a particular tissue or organ site. For example, the targeting moiety can be designed to or engineered to target the bone marrow, liver, spleen, pancreas, prostate, bladder, heart, lung, brain, skin, kidneys, ovaries, testis, lymph nodes, small intestines, large intestines, or stomach. It is understood and herein contemplated that there are a number of approaches that can target the therapeutic agent delivery vehicles disclosed herein to a target tissue or organ. Thus, specifically contemplated herein are therapeutic agent delivery vehicles can comprising any molecule that can be linked to the modified platelet for targeting a specific tissue or organ including, but not limited to peptides, polypeptides, polymers, nucleic acids, antibodies, sugars, or cells. In one aspect, for example, the targeting moiety targets the bone marrow and the moiety is selected from the group consisting of hematopoietic stem cell, a peptide comprising repeats of Asp or Glu, or bone marrow targeting formulation.

It is understood and herein contemplated that the drug or drug carrier (such as, for example, a modified and/or engineered platelet synthetic microparticles, synthetic nanoparticles, and/or cell-derived particles) of the disclosed therapeutic agent delivery vehicles can be linked to the targeting moiety through a chemical linkage or conjugation. In one aspect, disclosed herein are therapeutic agent delivery vehicles of any preceding aspect, wherein the platelet is chemically conjugated to the targeting moiety via copper(I) catalyzed [3+2] azide-alkyne cycloaddition (CuAAC), strain-promoted azide-alkyne cycloaddition (SPAAC), Strain-promoted alkyne-nitrone cycloaddition (SPANC), or Dibenzocyclooctyl (DBCO) Copper-Free cycloaddition (for example, a Dibenzocyclooctyl (DBCO)-polyethylene glycol (PEG) 4 NHS ester). To facilitate the conjugation, the targeting moiety can also be modified to complete the linkage to the platelet. Accordingly, disclosed herein are therapeutic agent delivery vehicles of any preceding aspect, wherein the targeting moiety is treated with an activated azide molecule (such as, for example, N-azidoacetylgalactosamine-tetraacylated (Ac4GalNAz)).

In one aspect, it is understood that the therapeutic agent delivery vehicles disclosed herein are intended for administration to a subject to treat, prevent, inhibit, or reduce a cancer or metastasis or to treat, prevent, inhibit, or reduce a relapse or metastasis following surgical recision (i.e., resection). Thus, disclosed herein are therapeutic agent delivery vehicles of any preceding aspect, wherein the therapeutic agent cargo comprises an antibody, small molecule, peptide, polypeptide, peptide mimetic, polymer, or nucleic acid. For example, the therapeutic agent cargo can comprise an immune checkpoint inhibitor such as for example, a PD-1 inhibitor, a PD-L1 inhibitor, or CTLA-4 inhibitor (such as, for example, nivolumab, pembrolizumab, pidilizumab, BMS-936559, Atezolizumab, Durvalumab, or Avelumab).

Contemplated herein are linkers for attaching the therapeutic agent cargo to the platelet of the disclosed therapeutic agent delivery vehicles. It is understood and herein contemplated that the linker can comprise any linker sufficient to link the therapeutic cargo to the platelet including 4-mercaptovaleric acid, 6-maleimidocaproic acid, sulfosuccinimidyl-4-(N-maleimidomethyl)-cyclohexane-1-carboxylate (Sulfo-SMCC), polyglycine (e.g. 3, 4, or 5 glycine), a polyserine (e.g. 3, 4, or 5 serine), or a combination of glycine and serine including repeating combinations. For example, the linker can be a glycine and serine linker, such as, for example, a G4S, GSG4, G2SG3SG2, G2SG, G3S linker, or any other linker known in the art where the base linker sequence can optionally be repeated 2, 3, 4, or more times. Thus, in one aspect, disclosed herein are therapeutic agent delivery vehicles of any preceding aspect, wherein the immune checkpoint inhibitor is attached to the surface of the modified platelet via a sulfosuccinimidyl-4-(N-maleimidomethyl)-cyclohexane-1-carboxylate (Sulfo-SMCC) linker.

1. Pharmaceutical Carriers/Delivery of Pharmaceutical Products

In one aspect, it is understood that the therapeutic agent delivery vehicles disclosed herein are intended for administration to a subject to treat, prevent, inhibit, or reduce a cancer or metastasis or to treat, prevent, inhibit, or reduce a relapse or metastasis following surgical recision (i.e., resection). Thus, disclosed herein are pharmaceutical compositions comprising the therapeutic agent delivery vehicles disclosed herein. For example, disclosed herein are pharmaceutical compositions comprising therapeutic agent delivery vehicles comprising a modified platelet and a targeting moiety; wherein the platelet has been modified to comprise a therapeutic agent cargo and a chemical linkage; and wherein the platelet is chemically conjugated to the targeting moiety.

The one or more therapeutic agents can be provided in the pharmaceutical composition along with the therapeutic agent delivery vehicles. Thus, in one aspect, disclosed herein are pharmaceutical compositions comprising therapeutic agent delivery vehicles comprising a modified platelet and a targeting moiety; wherein the platelet has been modified to comprise a therapeutic agent cargo and a chemical linkage; wherein the chemical linkage comprises Dibenzocyclooctyl (DBCO)-polyethylene glycol (PEG) 4 NHS ester; and wherein the platelet is chemically conjugated to the targeting moiety; wherein the one or more therapeutic cargo agents comprise, a small molecule (including, but not limited to 1-methyl-tryptophan (1-MT), norharmane, rosmarinic acid, epacadostat, navooximod, doxorubicin, tamoxifen, paclitaxel, vinblastine, cyclophosphamide, and 5-fluorouracil), siRNA, peptide, polymer, peptide mimetic, and/or antibody (such as, for example, and anti-PDL-1 antibody including, but not limited to nivolumab, pembrolizumab, pidilizumab, BMS-936559, Atexolizumab, Durvalumab, and Avelumab).

As the disclosed pharmaceutical compositions comprising the disclosed therapeutic agent delivery vehicles can be used to treat cancer it is further contemplated therein that the disclosed pharmaceutical compositions can further comprise any known any chemotherapeutic known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate).

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmic ally, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

2. Method of Treating Cancer

As noted herein, the disclosed therapeutic agent delivery vehicles, and/or pharmaceutical compositions can be used to treat any disease where uncontrolled cellular proliferation occurs such as cancers. Accordingly, in one aspect, disclosed herein are methods of treating, reducing, inhibiting, or preventing a cancer (including, but not limited to melanoma, renal cell carcinoma, non-small cell lung carcinoma, and/or bladder cancer); proliferation of a cancer (including, but not limited to melanoma, renal cell carcinoma, non-small cell lung carcinoma, and/or bladder cancer); metastasis of a cancer (including, but not limited to melanoma, renal cell carcinoma, non-small cell lung carcinoma, and/or bladder cancer); and/or treating, reducing, inhibiting, or preventing relapse, proliferation or metastasis of a cancer following surgical recision of a tumor (including, but not limited to melanoma, renal cell carcinoma, non-small cell lung carcinoma, and/or bladder cancer) in a subject comprising administering to a patient with a cancer therapeutic agent delivery vehicles, and/or pharmaceutical composition disclosed herein. Thus, in one aspect, disclosed herein are methods of treating, reducing, inhibiting, or preventing a cancer; proliferation of a cancer; metastasis of a cancer; and/or treating, reducing, inhibiting, or preventing relapse, proliferation or metastasis of a cancer following surgical recision of a tumor in a subject comprising administering to a subject therapeutic agent delivery vehicles comprising a modified platelet and a targeting moiety (or a pharmaceutical composition comprising the same). It is understood that the therapeutic agent delivery vehicles, and/or pharmaceutical compositions used in the disclosed methods can further comprise one or more therapeutic agents to enhance the immunotherapeutic effect of the therapeutic agent delivery vehicles, and/or pharmaceutical composition. For example, the therapeutic agent delivery vehicles, and/or pharmaceutical compositions used in the disclosed methods can further comprise a small molecule (including, but not limited to 1-methyl-tryptophan (1-MT), norharmane, rosmarinic acid, epacadostat, navooximod, doxorubicin, tamoxiten, paclitaxel, vinblastine, cyclophosphamide, and 5-fluorouracil), siRNA, peptide, peptide mimetic, or antibody (such as, for example, and anti-PDL-1 antibody including, but not limited to nivolumab, pembrolizumab, pidilizumab, BMS-936559, Atexolizumab, Durvalumab, and Avelumab). The one or more therapeutic agents can be encapsulated in or chemically linked to in the therapeutic agent delivery vehicles or supplied in the pharmaceutical composition along with therapeutic agent delivery vehicles. Accordingly, disclosed herein are methods of treating, reducing, inhibiting, or preventing a cancer; proliferation of a cancer; metastasis of a; and/or treating, reducing, inhibiting, or preventing relapse, proliferation or metastasis of a cancer following surgical recision of a tumor in a subject comprising administering to a subject therapeutic agent delivery vehicles comprising a modified platelet and a targeting moiety (or a pharmaceutical composition comprising the same), wherein the therapeutic agent cargo comprises a small molecule (including, but not limited to 1-methyl-tryptophan (1-MT), norharmane, rosmarinic acid, epacadostat, navooximod, doxorubicin, tamoxifen, paclitaxel, vinblastine, cyclophosphamide, and 5-fluorouracil), siRNA, peptide, peptide mimetic, or antibody (such as, for example, and anti-PDL-1 antibody including, but not limited to nivolumab, pembrolizumab, pidilizumab, BMS-936559, Atexolizumab, Durvalumab, and Avelumab).

It is understood and herein contemplated that the chemotherapeutic used in the disclosed cancer treatment, inhibition, reduction, and/or prevention methods can comprise any chemotherapeutic known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate).

Accordingly, disclosed herein are methods of treating, reducing, inhibiting, or preventing a cancer; proliferation of a cancer; metastasis of a; and/or treating, reducing, inhibiting, or preventing relapse, proliferation or metastasis of a cancer following surgical recision of a tumor in a subject comprising administering to a subject therapeutic agent delivery vehicles comprising a modified platelet and a targeting moiety; wherein the platelet has been modified to comprise a therapeutic agent cargo and a chemical linkage; wherein the platelet is chemically conjugated to the targeting moiety; further comprising administering to the subject separately or in the same composition any chemotherapeutic known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Amboclorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Said methods can also include the administration of any of the therapeutic agents disclosed herein including but not limited to a small molecule (including, but not limited to 1-methyl-tryptophan (1-MT), norharmane, rosmarinic acid, epacadostat, navooximod, doxorubicin, tamoxifen, paclitaxel, vinblastine, cyclophosphamide, and 5-fluorouracil), siRNA, peptide, peptide mimetic, or antibody (such as, for example, and anti-PDL-1 antibody including, but not limited to nivolumab, pembrolizumab, pidilizumab, BMS-936559, Atexolizumab, Durvalumab, and Avelumab).

As noted above, the disclosed methods or useful in the treatment of cancer. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer In one aspect, the disclosed methods of treating a cancer comprising administering to a subject any of therapeutic agent delivery vehicles or pharmaceutical compositions disclosed herein can comprise administration of the therapeutic agent delivery vehicles or pharmaceutical compositions at any frequency appropriate for the treatment of the particular cancer in the subject. For example, therapeutic agent delivery vehicles or pharmaceutical compositions can be administered to the patient at least once every 12, 14, 16, 18, 20, 22, 24, 26, 28, 30, 32, 34, 36, 38, 40, 42, 44, 46, 48 hours, once every 3, 4, 5, 6, 7, 8, 9, 10, 11, 12, 13, 14, 15, 16, 17, 18, 19, 20, 21, 22, 23, 24, 25, 26, 27, 28, 29, 30, 31 days, once every 2, 3, 4, 5, 6, 7, 8, 9, 10, 11, or 12 months. In one aspect, the therapeutic agent delivery vehicles or pharmaceutical compositions are administered at least 1, 2, 3, 4, 5, 6, 7 times per week.

In one aspect, the amount of the therapeutic agent delivery vehicles, or pharmaceutical compositions disclosed herein which are administered to the subject for use in the disclosed methods can comprise any amount appropriate for the treatment of the subject for the particular cancer as determined by a physician. For example, the amount of the therapeutic agent delivery vehicles, or pharmaceutical composition can be from about 10 mg/kg to about 100 mg/kg. For example, the amount of the therapeutic agent delivery vehicles, or pharmaceutical composition administered can be at least 10 mg/k, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, or 100 mg/kg. Accordingly, in one aspect, disclosed herein are methods of treating a cancer in a subject, wherein the dose of the administered therapeutic agent delivery vehicles, or pharmaceutical composition is from about 10 mg/kg to about 100 mg/kg.

C. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: PD-1 Blockade Cellular Vesicles for Cancer Immunotherapy a) Results
(1) Engineering Platelet Decorated with aPD1

Platelets were collected from the whole mice blood and treated with prostaglandin E1 (PGE1) to inhibit the platelet activation. aPD1 was conjugated to the platelets using sulfosuccinimidyl-4-(N-maleimidomethyl)-cyclohexane-1-carboxylate (SMCC) as a linker through a covalent conjugation method. Both flow cytometry analysis and confocal images confirmed the successful decoration of aPD1 on the platelets. Further, the conjugation amount of aPD1 on the platelets was quantified using the enzyme-linked immunosorbent assay (ELISA), which showed that the maximum conjugation amount of aPD1 was achieved as ~0.3 pg per platelet (FIG. 3A). Such coupling showed negligible cytotoxicity and did not induce the lysis of platelets, which was confirmed by the integrity of platelets after 24 h (FIG. 3B). In addition, we characterized the functionality of platelets via collagen binding and platelets aggregation. The P-aPD1 efficiently bound to collagen, with insignificant difference when compared with native platelets. Both platelets and P-aPD1 aggregated after activation, indicating that aPD1 conjugation did not alter platelet functionality. Furthermore, it was validated that after activation, a remarkable amount of aPD1 was released due to the generation of PMPs, which was significantly higher than the non-activated platelets, indicating the well preserved biofunctionality after decoration of aPD1 (FIG. 3C).

(2) Integration of HSC with Platelets

HSCs were isolated from the femur and tibia of C57B6 mice and cultured in 40 µM $Ac_4GalNAz$ containing medium for 72 h. $Ac_4GalNAz$ has been identified to label numerous cells through N-acetylgalactosamine (GalNAc) metabolism and incorporation into mucin-type O-linked glycoproteins. The cell viability study confirmed insignificant cytotoxicity of $Ac_4GalNAz$ at the studied concentration. The presence of azide groups on the surface of HSC was determined by the addition of an alkynyl-based probe, FAM alkyne. The flow cytometry analysis showed increased fluorescence signal on $Ac_4GalNAz$-treated HSCs when reacted with FAM alkyne through a click reaction, which was significantly higher than that of the HSC control. Furthermore, the $Ac_4GalNAz$-treated HSCs displayed a bright fluorescence under confocal observation, while no fluorescence signal was found on HSC control.

Next, the platelets were conjugated with dibenzocyclooctyne-$PEG_4$-N-hydroxysuccinimidyl ester (DBCO-$PEG_4$-NHS ester), which can react with the amine groups on the platelet surface. The successful decoration of DBCO-$PEG_4$-NHS ester was determined by the covalent attachment of an azide-based fluorescence probe, azide-fluor 488. The flow cytometry analysis showed brighter fluorescence signals in DBCO-$PEG_4$-NHS ester-treated platelets than that in non-treated platelets and platelets physically mixed with azide probe.

To decorate the HSCs with platelets through the click reaction, DBCO-$PEG_4$-NHS ester-treated platelets were subjected to the azide-incorporated HSCs and incubated for 45 min. To avoid the aggregation of platelet-HSC assembly, excessive azide-PEG was added to block the free DBCO groups on the platelets. As seen from the confocal and scanning electron microscope (SEM) images, a direct decoration at the cell-cell interface was clearly observed and the cellular conjugation was precisely tuned at 1:1 ratio (platelet:HSC), which can be attributed to the cell-cell steric hindrance (FIG. 1B). Additionally, both HSC and platelet morphologies were well maintained after conjugation. The platelet function was well preserved, as evidenced by preservation of several key proteins and generation of platelet-derived microparticles after activation (FIG. 1C). To further investigate the effect from numbers of conjugated platelets on the surface of HSC, the reaction ratio of platelets to HSCs was increased and the numbers of platelets bound on the HSCs quantified. At the ratio of 1:1 (platelet:HSC), the majority of the assemblies were one platelet on one HSC (about 66%). With the increased platelet numbers, the conjugated platelets on the surface of HSCs were increased correspondingly. At the ratio of 8:1, over 80% HSCs was bound with more than three platelets (FIGS. 1D and 1E). However, the HSC viability decreased along with the increased numbers of conjugated platelets. Therefore the reaction ratio of 1:1 (platelet:HSC) was selected for the following studies.

(3) In Vivo Treatment Efficacy of S-P-aPD1

The retention of residual leukemia cells in the bone marrow is one of the main reasons for AML relapse. Thus, the accumulation of drug delivery system in bone marrow to eliminate the leukemia cells is crucial for the enhanced anti-leukemia effect. To investigate the bone marrow homing capability of S-P-aPD1, the in vivo pharmacokinetics of S-P-aPD1 was first evaluated. As shown in FIG. 4A, S-P-aPD1 displayed a significantly longer half-life time than that of free aPD1, which can be ascribed to the long persistence in the circulation time of HSCs with platelets. The quick clearance of free aPD1 can be attributed to the high immunogenicity of rat anti-mouse IgG. The bone marrow homing capability of S-P-aPD1 was then tested. aPD1 was labeled with Cy5.5 and conjugated to HSC, platelet, and HSC-platelet, respectively. Free aPD1, HSC-aPD1 (designated as S-aPD1), platelet-aPD1 (designated as P-aPD1), HSC and platelet-aPD1 mixture (designated as S+P-aPD1) and S-P-aPD1 were intravenously injected into C57B6 mice at the equivalent aPD1 dose and the leg bone were taken out for imaging after 6 h. Both S-aPD1 and S-P-aPD1 showed higher fluorescence signals at the bone marrow than P-aPD1, S+P-aPD1 mixture, and free aPD1 group, which indicated the superior bone marrow accumulation capability of HSCs (FIG. 4B). The quantitative results showed over 25-fold greater fluorescence signal from bone tissues in S-aPD1 and S-P-aPD1-treated mice than other groups (FIG. 4C). Moreover, the simple blend of HSC and P-aPD1 did not enhance the accumulation of aPD1 at the bone marrow. The bone marrow accumulation of HSC-platelet assembly was further confirmed by fluorescence imaging, as evidenced by the co-localization of HSC (green fluorescence) and platelet (red fluorescence) in the bone marrow, and demonstrated the preservation integrity of the membranes of both HSC and platelets localized within the bone marrow. Furthermore, the fluorescence signals of PMPs were found in the bone marrow treated with HSC-platelets, whereas insignificant PMPs were observed in platelet and PMPs groups. The existence of PMPs suggested the in situ potential generation of PMPs in the bone marrow after treatment with HSC-platelets, which might be triggered by the leukemia microenvironment in the bone marrow.

To investigate the treatment efficacy of S-P-aPD1 toward AML, the C1498 cells were intravenously injected into the C57B6 mice. The surface expression of PD-L1 on C1498 cells after administration was confirmed by flow cytometry. C1498 leukemia-bearing mice were treated with three doses of saline, HSCs, platelets, free aPD1, S-aPD1, P-aPD1, S+P-aPD1 and S-P-aPD1 every other day after one week at the aPD1 dose of 0.5 mg/kg (FIG. 4D). In addition, another group of mice were treated with daily administration of aPD1 for 6 days (aPD1 dose, 0.25 mg/kg). The growth of leukemia was monitored via the bioluminescence signal of C1498 cells. As shown in FIGS. 4E and 4F, the mice treated with S-P-aPD1 displayed a decreased bioluminescence signal after two weeks, and the bioluminescence signal completely disappeared after three weeks. Furthermore, the 7 of 8 mice in this group displayed strong immune response without any detectable leukemia cell signals. In contrast, the mice treated with aPD1 did not show enhanced immune effects regarding survival time due to the quick clearance and non-specific biodistribution of aPD1. The modest treatment efficacy of P-aPD1 groups can be attributed to the lack of bone marrow homing capability of platelets. Further, the insignificant immune response in S-aPD1 group can be ascribed to the inefficient activation of T cells due to the steric hindrance of cell-cell interaction. In contrast, the S-P-aPD1 with bone marrow homing capability can effectively accumulate in the bone marrow and release the aPD-1 efficiently to prime T cells. The mouse survival rate, which was correlated with the growth of leukemia, was about 87.5% after 80 days for the mice receiving S-P-aPD1. In contrast, no mice survived beyond 40 days for all other aPD1 treatments and beyond 30 days for the saline group (FIG. 4H). The C1498 cells in the peripheral blood were also analyzed using flow cytometry. As shown in FIG. 4G, the mice receiving S-P-aPD1 treatment displayed the insignificant amount of C1498 cells, which was significantly lower than other aPD1 treatment groups and the saline control.

Further, the spleens of the mice receiving different treatments were resected and imaged (FIG. 4I). The spleens from the S-P-aPD1-treated mice displayed a normal morphology whereas the other treatment groups had large spleen sizes. The quantitative results showed the smallest weight of spleen from the mice treated with S-P-aPD1 that was ½~⅓ of other spleens (FIG. 4J). Hematoxylin and eosin (H&E) staining was then used to investigate the development of leukemia in main organs. The presence of the leukemia cells was found in the bone marrow, liver, spleen and lung tissues for the mice treated with saline. Whereas, the mice treated with S-P-aPD1 displayed negligible amount of leukemia cells in the main organs. Particularly, the immune function zone in the spleen of the mice treated with saline was almost destroyed by leukemia cells, which could lead to the ineffective immune response.

(4) T Cell-Mediated Immune Response

To understand the cellular mechanisms underlying the observed therapeutic efficacy of S-P-aPD1 treatment, the T cells in the peripheral blood upon treatment were harvested and analyzed by flow cytometry. Approximately 4-fold increase in CD3+ T cells was observed in mice receiving the S-P-aPD1 treatment, as compared to saline, HSCs and platelets treated control groups (FIGS. 5A and 5C). CD3+ T cells in S-P-aPD1 treatment groups showed a 1.9-2.4-fold increase when compared to other aPD1 treatment groups (FIGS. 5A and 5C). Moreover, mice receiving S-P-aPD1 treatment displayed a 1.5-fold increase in CD8+ T cells when compared to saline, HSCs and platelets control groups and approximate 1.3-fold increase as compared to other aPD1 treatment groups (FIGS. 5B, and 5D). Furthermore, The IFNγ+CD8+ T cells in S-P-aPD1 treatment groups were 1.9-2.6-fold increase when compared to other aPD1 treatment groups and 6.4-17.8-fold increase as compared to saline, HSCs and platelets control groups. These increases in CD3+, CD8+ and IFNγ+CD8+ T cells were consistent with the inhibition of the growth of leukemia, substantiating the effective immune response in S-P-aPD1 group and priming of cytotoxic T cells. T cell subsets in the bone marrow were further analyzed. PD-1-expressing T cells were detected in the bone marrow of leukemia-bearing mice by flow cytometry. Mice receiving S-P-aPD1 treatment displayed 1.8-1.9-fold increases in CD8+ T cells as compared to saline, HSC and platelet control groups, and approximate 1.3-fold increase as compared to other treatment groups with aPD1. Moreover, the CD8+ T cells in the bone marrow of mice after treated with S-P-aPD1 displayed about 44% percentage of GzmB positive (FIG. 6), which was significantly higher than other treatment groups, suggesting that the effector T cells were increased after S-P-aPD1 treatment. Besides, the effector T cells in early activation status in S-P-aPD1 treatment group were higher than other treatment groups, as evidenced by higher percentages of CD8+CD44+CD69+ and CD8+CD44+CD25+ T cells. IFNγ+CD8+ T cells in S-P-aPD1 treatment group were 2.6-2.9-fold increases as compared to other aPD1 treatment groups and 5.3-21.2-fold increases as compared to saline, HSC and platelet control groups. In contrast, CD8+ and IFNγ+CD8+ T cell subsets in the bone marrow of non-leukemia bearing mice did not showed significant increase after treated with S-P-aPD1. Luminex-based quantification of cytokines and chemokines revealed the four clusters of co-regulated proteins, with many pro-inflammatory factors increased in the peripheral blood after treatment with aPD1 treatments (FIG. 5E). Furthermore, the majority of the cytokines and chemokines were highly up-regulated in S-P-aPD1 group compared to other aPD1 treatment groups, which was consistent with the superior anti-leukemia treatment efficacy of S-P-aPD1. The increased serum cytokines level might reflect the alteration of other immune cell subsets including monocytes and myeloid cells, as AML was characterized by the prevention of mature of monocytes and myeloid cells. The development of leukemia could potentially cause the abnormalities of monocytes and other myeloid cells including granulocyte in AML patients as demonstrated by previous studies To further confirm the long-term potency of S-P-aPD1 treatment, the CD8+ T cells were isolated and analyzed via flow cytometry. Besides the shift of native CD8+ T cells to active phenotype, there is also a shift to central memory CD8+ T cell phenotype. The CD44$^+$CD62L$^+$ central memory phenotype is 2.1-fold higher than the saline control (FIG. 7A). Similarly, the CD44$^{hi}$CD122$^{hi}$ memory T cell subset was also increased. The functionality of the memory subsets in S-P-aPD1 treated mice was demonstrated in re-challenge experiments. Next, the mice receiving S-P-aPD1 treatment were re-challenged with $1 \times 10^6$ C1498 cells at 80 days after leukemia inoculation. The results showed that previously treated, leukemia-free mice were resistant to the newly administered leukemia cells and remained leukemia free at 60 days, whereas such leukemia grew robustly in the native mice (FIGS. 7B and 7C). In native mice group, all the animals died within 40 days. These results indicated a long-term anti-leukemian immune response induced by the S-P-aPD1 treatment. To further confirm the key role of T cells-mediated immune response in S-P-aPD1 treatment, T cell-knockout mice (rag$^{-/-}$) were injected with C1498 cells and then administered with S-P-aPD1. As shown in FIG. 7D, all the animals died within three weeks in the saline group. Furthermore, free aPD1 and S-P-aPD1 treatment did not offer any significant inhibition on growth of leukemia or survival benefit over the saline control, indicating the T cell-mediated immune response in aPD1-based treatment. Considering S-P-aPD1's ability to shift the phenotype of CD8+ T-cell, efforts mere made to determine whether the observed anti-leukemia effect depends on the CD8+ T cells. Mice bearing C1498 leukemia cells were depleted of CD8+ T cells via intraperitoneal administration of anti-CD8 monoclonal antibodies. The complete depletion of CD8+ T cells was confirmed by flow cytometry analysis. The therapeutic effect of the S-P-aPD1 was abrogated in the absence of CD8+ T cells. No mice receiving saline, free aPD1 and S-P-aPD1 survived beyond 40 days, indicating that the CD8+ T cells are essential for producing anti-leukemia effects from S-P-aPD1 treatments (FIG. 7E). The treatment efficacy of S-P-aPD1 was also investigated in PD1 knockout mice model (PD$^{-/-}$). A significantly diminished anti-leukemia effect was found in PD1 knockout mice with insignificant survival benefits, validating the importance of PD1 blockage in PD1-mediated immune response (FIG. 7F).

To assess the effectiveness of S-P-aPD1 in treating another type of leukemia, we used the WEHI-3 myelomonocytic leukemia cell line in BALB/cJ mice. In this leukemia model, mice receiving S-P-aPD1 therapy showed better leukemia control, and 62.5% of the treated mice were alive at day 50. In contrast, mice in control groups succumbed by day 40 and displayed larger spleens.

In summary, this study presents a new "cell combination" drug delivery approach—one cell for targeting and the other for active release, to achieve effective immune responses for the complete elimination of leukemia cells. By taking advantage of HSC homing capability and in situ activation of platelets, S–P-aPD1 can enhance the delivery and effectiveness of aPD1 in the bone marrow, thereby effectively priming T cells and inhibiting the growth and recurrence of leukemia. Such S–P-aPD1 can induce potent immune response while mitigating toxicity compared with traditional non-selective cytotoxic agents for AML. Moreover, the S–P-aPD1 delivery system can minimize the immunogenicity and side effects since the constituents are derived from patients themselves. Due to excellent biocompatibility and ease of manufacturing, this newly developed biotechnological cell-engineering approach for delivering immune checkpoint inhibitor represents an attractive platform for clinical translation. Furthermore, this cell assembly-mediated delivery strategy can be adopted to incorporate other bio-particulates for treating a variety of diseases, for which spatiotemporal drug delivery is essential.

b) Materials and Methods (1) Cell Lines.

The mouse leukemia cell line, C1498, was kindly provided by Dr. Bruce Blazar at the University of Minnesota. The C1498 cells were maintained in Dulbecco's Modified Eagle's Medium (DMEM) medium (Gibco, Invitrogen, Carlsbad, CA) supplemented with 10% fetal bovine serum (Invitrogen), 100 U/mL penicillin (Invitrogen) and 100 U/mL streptomycin (Invitrogen). The HSCs and progenitor cells (designated as HSCs in the all studies) were isolated from femur and tibia of C57BL/6J mice. Bone marrow was first pre-enriched with a lineage depletion kit (Miltenyi, Germany). The resulted cells were subsequently treated with anti-Sca-1 microbeads kit (Miltenyi) to obtain lin$^-$ Sca-1$^+$ HSCs. Cells were cultured in Serum-Free Expansion Medium (SFEM, STEMCELL Technologies, Cambridge, MA) with addition of human IL-6 (50 ng/mL, Thermo Scientific), human Flt3 ligand (100 ng/mL, Thermo Scientific), murine stem cell factors (SCF, 50 ng/mL, Thermo Scientific) and Low-density lipoprotein (LDL, 40 μg/mL, Thermo Scientific). Cells were cultured in an incubator (Thermo Scientific) at 37° C. under an atmosphere of 5% $CO_2$ and 90% relative humidity. The cells were sub-cultivated approximately every 2-3 days at 80% confluence at a split ratio of 1:3.

(2) Antibody.

The anti-PD1 antibody (aPD1) was obtained from Biolegend (cat. no. 114114, Clone: RMP1-14). The antibodies used for immunostaining were specific for CD3 (Biolegend, cat. no. 100236, Clone: 17A2), CD4 (BD Bioscience, cat. no. 553046, Clone: RM4-5), CD8a (Biolegend, cat. no. 100708, Clone: 53-6.7), IFN-γ (Biolegend, cat. no. 505806, Clone: XMG1.2), CD122 (Biolegend, cat. no. 123207, Clone: TM-(31), CD41 (Biolegend, cat. no. 133904, Clone: MWReg30), CD9 (Biolegend, cat. no. 124807, Clone: MZ3), CD61 (Biolegend, cat. no. 104307, Clone: 2C9.G2 (HMβ3-1), CD62P (Biolegend, cat. no. 148305, Clone: RMP-1), CD36 (Biolegend, cat. no. 102605, Clone: HM36), CD154 (Biolegend, cat. no. 106505, Clone: MR1), CD62L (Biolegend, cat. no. 104405, Clone: MEL-14), CD44 (Biolegend, cat. no. 103024, Clone: IM7), CD34 (Biolegend, cat. no. 128609, Clone: HM34), CD38 (BD Bioscience, cat. no. 558813, Clone: 90/CD38), CD117 (Biolegend, cat. no. 105812, Clone: 2B8), CD366 (BD Bioscience, cat. no. 566346, Clone: 5D12/TIM-3), CD223 (Biolegend, cat. no. 125207, Clone: C9B7W), CD274 (Biolegend, cat. no. 124311, Clone: 10F.9G2), Granzyme B (GzmB) (Biolegend, cat. no. 372204, Clone: QA16A02), CD25 (Biolegend, cat. no. 101904, Clone: 3C7), CD69 (Biolegend, cat. no. 104508, Clone: H1.2F3). The cells after staining were subjected to fluorescence-activated cell sorting (FACS) analysis following the manufacturers' instructions. Multicolor flow cytometry was used with appropriate compensation. All antibodies were used following manufacture's instruction. The fluorochromes conjugated on the antibody were exactly matched to the same fluorochromes channel After staining, cells were analyzed on a FACS Calibur instrument (Cytoflex, BD), using the FlowJo or Cytexpert software package. CD8+ T cell depletion antibody (Clone: YTS169.4) was purchased from BioXCell. The rat IgG was purchased from Invitrogen. Recombined mPD-1 was obtained from R&D systems. The secondary antibodies used for immunostaining were goat anti-rat IgG (H+L; Thermo Fisher Scientific, cat. no. A18866).

(3) Mice.

CS7BL/6J mice, T cell knockout mice (B6.129S7-Rag1$^{tm-Mom}$/J) and PD1 knockout mice (B6.Cg-Pdcd1$^{tm1.1Shr}$/J) were purchased from Jackson lab. All the animal studies were strictly following the animal protocol approved by the Institutional Animal Care and Use Committee at the University of North Carolina at Chapel Hill and North Carolina State University.

(4) Preparation of aPD1 Conjugated Platelets.

Murine platelets were isolated from whole mouse blood. Briefly, whole blood was collected from the C57BL/6J mice (non-terminal collection from the orbital sinus) with dipotassium EDTA-treated tubes containing 1.0 mL citrate-phosphatedextrose (16 mM citric acid, 90 mM sodium citrate, 16 mM $NaH_2PO_4$, 142 mM dextrose, pH 7.4). The platelet-rich plasma (PRP) was then collected by centrifuging the whole blood at 100 g for 20 min at room temperature. Thereafter, prostaglandin E1 (PGE1) was added to platelet-rich plasma at a final concentration of 1 μM and PRP was centrifuged for another 20 min at 100 g to further get rid of red blood cells. To isolate the platelets, the platelet-rich plasma was centrifuged at 800 g for 20 min. Next, the pellet was collected and resuspended in PBS buffer containing 1 mM EDTA and 1 μM PGE1. For the in vitro activation of platelets, the platelet solution was centrifuged at 800 g for 20 min and suspended in PBS buffer. The number of platelets were counted using hemocytometer under microscope.

To decorate aPD1 (Biolegend) on the surface of platelet through a sulfosuccinimidyl-4-(N-maleimidomethyl)-cyclohexane-1-carboxylate (Sulfo-SMCC, Pierce) linker, the free thiol groups on the surface of platelets were first examined using flow cytometry. Briefly, 1×10$^6$ platelets were mixed with 0.1 mg/mL maleimide fluorescence probe (Mal-FITC, sigma) in PBS and centrifuged at 800 g for 10 min after 15 min reaction. The platelets were then washed, centrifuged and subjected to flow cytometry. Red blood cells that have been reported to have minimal free thiol groups were used as the control group here. Next, aPD1 was reacted with Sulfo-SMCC at a molar ratio of 1:1.2 for 2 h at 4° C. The mixture was then centrifuged in an ultrafiltration tube (molecular weight cut-off=3 kDa) to discard the excess SMCC linker. Thereafter, SMCC-aPD1 was added into platelets and kept in room temperature for 1 h to obtain aPD1-platelets. The excess antibodies were removed by centrifugation at 800 g for 20 min. The pellet was washed and stored in PBS containing 1 μM PGE1 at room temperature prior to use in experiments. To further evaluate the aPD1 conjugation efficiency, various amounts of aPD1 was reacted with platelets as described above and the resulted aPD1-platelet was centrifuged, washed and lysed using ultrasonication. The amount of aPD1 conjugated to the platelets was measured via ELISA (rat IgG total ELISA kit, eBioscience). To evaluate the effects of aPD1 on the platelets, the stability of platelets was investigated by counting the amounts of platelets using microscope at 24 h post-reaction. To study the aPD1 release, 0.5 U/mL thrombin was added to $1\times10^8$ aPD1-platelet suspension (500 μL) to activate platelet at 37° C. At prearranged time intervals, 50 samples was collected and centrifuged at 800 g for 20 min and the supernatant was detected by ELISA. The non-activated aPD1-platelet was used as a control.

To further investigate the functionality of platelets after conjugation of aPD1, the collagen binding and platelet aggregation studies were performed. Murine collagen type I/III (Bio-Rad) was reconstituted to a concentration of 2.0 mg/mL, added to 96-well plate and incubated overnight at 4° C. The plate was further blocked with 2% BSA for 2 h and washed with PBS for collagen binding study. The blank plate was only blocked but without addition of collagen. $1\times10^7$ P-aPD1 or platelets stained with WGA Alexa Fluor 594 were added to platelets with or without collagen pre-coating. The plate was then washed with PBS after 1 min of incubation and subjected to confocal for imaging. For aggregation studies, P-aPD1 or platelets labeled with WGA Alexa Fluor 594 were incubated in complete medium with 0.5 U/mL thrombin, and then subjected to confocal imaging (CLSM, LSM 710, Zeiss).

To visualize the decoration of aPD1 on the surface of platelet, aPD1 was conjugated with FITC and platelet was stained with rhodamine. The aPD1-platelet was then observed via confocal laser scanning microscopy (CLSM, LSM 710, Zeiss). To further characterize the aPD1-platelet, the aPD1-platelet was stained with PE-stained rat anti-IgG antibody and subjected to flow cytometry. The unstained platelet and simple mixture of platelet and antibody were used as the controls.

(5) Preparation of HSC-Platelet-aPD1 Assembly.

HSCs were isolated from the femur and tibia of C57BL/6J mice and cultured in 40 μM Ac4GalNAz (Thermo Scientific) containing medium for 72 h. To detect the presence of azide group on the surface of HSCs, the HSCs were incubated with PBS containing 50 μM Copper(II)-TBTA complex, 2 mM sodium ascorbate, 25 μM FAM alkyne in the dark. After 15 min, the resulted HSCs were washed with PBS thrice and subjected to flow cytometry analysis and confocal observation. To functionalize the platelets with triple bond for click reaction, the platelets were treated with 20 μM dibenzocyclooctyne-$PEG_4$-N-hydroxysuccinimidyl ester (DBCO-NHS) for 30 min at room temperature and then decorated with aPD1 as described above. To examine the presence of triple bond on the platelets, the resulted platelets were reacted with 20 μM azide-FITC probe for 15 min in the dark and then subjected to flow cytometry analysis.

For conjugation of platelets to HSCs, $1\times10^7$ DBCO-functionalized platelets were added into $1\times10^7$ Ac4GalNAz-treated HSCs and incubated for 45 min at 37° C. Thereafter, excess azide-PEG (50 μM) were added into HSCs and platelets mixture and incubated for additional 15 mM to quench the additional DBCO on the surface of platelets. The resulted platelet-HSC assembly was observed via confocal microscopy. The platelets were stained with rhodamine for observation.

To investigate the conjugated amount of platelets on the surface of HSCs, the reacted amount of platelets were increased from 1:1 (ratio of platelet to HSC) to 8:1. After addition of excess of azide PEG, the resulted S-P-aPD1 was washed with PBS thrice and subjected to confocal microscope. The percentage of conjugated platelets on the HSCs were also quantified by counting 200 S-P-aPD1 assemblies at different reaction ratios.

For scanning electron microscope (SEM) characterization, the S-P-aPD1 was first fixed with 3.5% glutaraldehyde for 4 h, washed with PBS thrice, and then dehydrated with ethanol in a graded series (30%, 50%, 70%, 85%, 90% each time for 15 min and 100% twice for 30 min) and then treated with tert-butanol. After drying under vacuum, the S-P-aPD1 was coated with gold/palladium and examined on SEM (Verios 460L).

To test the bioactivity of platelets after conjugation on HSCs, the S-P-aPD1 was treated with 0.5 U/mL thrombin for 30 min at 37° C. and then centrifuged at 300 g for 5 min. The supernatant was collected, and stained with 2% uranyl acetate and observed with a transmission electron microscopy (TEM, JEOL 2000FX, Hitachi). The functionality of platelets on S-P-aPD1 was also detected by examination of key proteins expression on the platelets. Briefly, the S-P-aPD1 were stained with various rat anti-mouse antibodies (CD61, CD41, CD9, CD36, CD62P, CD154, Biolegend) and analyzed by flow cytometry. CD62P and CD154 detection was performed after addition of thrombin for platelet activation.

To test the viability of HSCs after conjugation, HSCs or S-P-aPD1 were seeded in the 96-well plates and added with 10 μL of the CCK8 solution (Dojindo, Japan) after 48 h incubation. Four hours later, the absorbance was measured at the wavelength of 450 nm by a microplate reader.

For conjugation of aPD-1 on the surface of HSC, $1\times10^6$ HSCs were reacted with SMCC-aPD1 stained with rhodamine at 4° C. for 1 h. After centrifugation at 400 g for 5 min, the HSC-aPD1 was incubated at 37° C. for 2 and 6 h. After stained with endo-lysosome tracker green, Hoechst 33258 and trypan blue, the HSC-aPD1 was subjected to confocal for observation.

(6) In Vivo Pharmacokinetics.

Six mice were randomly divided into two groups and intravenously injected with free aPD1 (aPD1, 1 mg/kg), S-P-aPD1 (aPD1, 1 mg/kg, HSC/platelets, $1\times10^8$, in 200 μL PBS for each mouse). At pre-determined time points, a 10 μL blood sample was collected from the tail, diluted in 100 μL water and subjected to sonication. The released aPD1 was measured by rat IgG total ELISA kit. For the in vivo biodistribution study, the mice were intravenously injected with Cy5.5-labelled free aPD1, S-aPD1, P-aPD1, mixture of HSC and aPD1, and S-P-aPD1. After 6 h, the bones were taken out and the fluorescence images of bones were recorded using an IVIS Spectrum system (Perkin Elmer). The fluorescence intensities of region-of-interests (ROI) were analyzed by Living Image Software. For bone marrow accumulation of HSC-platelet assembly, the leukemia-bearing mice were intravenously injected with HSC-platelet assembly (HSC stained with FITC, platelet stained with rhodamine, HSC/platelets, $5\times10^7$). At 12 h post-injection, the mice were euthanized. The bones were collected and sectioned. Bone tissues were fixed in the 10% formalin. After 48 h, bones were decalcified in EDTA solution for 2 days, followed by incubation in 30% sucrose. Thereafter, the bone tissues were frozen in O.C.T. medium for sectioning. After staining with Hoechst, the bone slides were subjected to confocal microscope for observation. To observe the potential generation of PMP in the bone marrow, the rhodamine-labeled platelets, PMPs and HSC-platelets were i.v. injected to the leukemia bearing mice. After 24 h, the bone tissues were collected, sectioned as described above and subjected for confocal observation. The quantification of the fluorescence signal was performed on Image J software.

(7) In Vivo Leukemia Treatment.

To build leukemia model, $1\times10^6$ luciferase-tagged C1498 cells were intravenously injected into mice. After 7 days, the 64 mice were randomly divided into 8 groups and intravenously administered with PBS, HSC, platelet, free aPD1, S-aPD1, P-aPD1, S+P-aPD1 and S–P-aPD1 at the cell numbers of $5\times10^7$ and aPD1 concentration of 0.5 mg/kg via tail vein. The treatment was repeated every other day for three times. The growth of leukemia was monitored by detection of bioluminescence signals from C1498 cells. D-luciferin (Xenogen) was used as a substrate for luciferase and each mouse was i.p injected with D-luciferin at the concentration of 150 mg/kg in 100 μL PBS. Bioluminescence images were collected after 5 min injection of D-luciferin with an IVIS Spectrum Imaging System (Perkin Elmer) and acquisition time of bioluminescence signal was 5 min. The bioluminescence signals were recorded at 1 week, 2 weeks and 3 weeks after C1498 cells injection. Living Image software version 4.3.1 (Perkin Elmer) was used to quantitate the bioluminescence signal. To correct for background bioluminescence, signals acquired from leukemia-free mice (injected with D-luciferin) were subtracted. After 3 weeks, a 100 μL blood sample was collected and lysed with red blood cells lysis buffer. The remaining cells were subjected to flow cytometry for investigation of amounts of C1498 cells in peripheral blood. Besides, the survival time of each mouse was recorded and the spleen was weighted and imaged. Furthermore, the main tissues (heart, liver, spleen, lung, liver, bone) were taken out for the hematoxylin and eosin (H&E) staining. The slides were observed by optical microscope (DM5500B, Leica).

To investigate the cellular mechanism underlying the treatment efficacy of S–P-aPD1, T cell knockout mice ($rag^{-/-}$), CD8+ T cell depleted mice and PD1 knockout mice ($PD^{-/-}$) were injected with saline, free aPD1 and S–P-aPD1 at aPD1 concentration of 0.5 mg/kg. The survival time of each mouse was recorded. To deplete CD8+ T cells, C57BL/6J mice were injected with 500 μg of anti-CD8 mAbs (clone YTS 169.4, Bio X Cell) intraperitoneally every 72 h beginning 2 day prior to S–P-aPD1 treatment for the duration of the treatment. Depletion was confirmed by the flow-cytometry analysis of T cells isolated from peripheral blood (CytoFlex, Beckman Coulter, USA). All the flow-cytometry data were analyzed by the CytExpert software.

For leukemia re-challenge study, the C57BL/6J mice were injected with $1\times10^6$ C1498 cells after 80 days of first C1498 cells injection. The bioluminescence signals were monitored weekly and survival time was recorded.

(8) Cytokine and Chemokine Detection and T Cell Analysis.

The plasma levels of multiple cytokines and chemokines were measured using Luminex-based detection. Peripheral blood was harvested at day 12 and then centrifuged at 300 g for 10 min. The supernatant were aliquoted and stored at −80° C. until analysis. Samples were diluted with Luminex assay buffer and followed manufacturer's instructions. Cytokine values were Z-score normalized per-sample before clustering. Samples were divided into four groups arbitrarily based on their cytokine profile by k-means clustering, using the heatmap function. To investigate the PD-1 expression in T cells in the bone marrow, the bone marrow was collected and stained with anti-CD8 and anti-PD1 antibodies (events collected for analysis were $5\times10^4$). The anti-human CD8 antibody was used for isotype control antibody. For T cell analysis, peripheral blood and bone marrow was harvested at day 12. The blood sample was lysed first by red blood cell lysis buffer and then stained with anti CD3, anti CD8, anti CD4, anti Granzyme B, anti CD44, anti CD25, anti CD69 and anti IFNγ antibodies for 30 min. The Granzyme B staining was performed according to Biolegend intracellular staining protocol. For counting CD3+ T cell number, 150 μL blood was lysed first by red blood cell lysis buffer and subjected to flow cytometry analysis after stained with APC-anti-CD3 antibody with addition of 50 μL counting beads. The events collected were $1\times10^5$ for CD8 and CD4 analysis and $5\times10^4$ for IFNγ analysis. For memory T cell analysis, the splenocytes were taken out from the saline-treated mice and S–P-aPD1 treated mice after 30 days and stained with anti CD8, anti CD44, anti CD62L and anti CD122 antibody. Thereafter, the stained cells were subjected to flow cytometry for analysis (events collected for analysis were $5\times10^4$). To detect the T cells exhaustion in $PD^{-/-}$ mice, the lymphocytes of lymph nodes from normal mice and $PD^{-/-}$ mice were collected, stained with anti-CD8, anti-TIM-3, and anti-LAG-3 and subjected to flow cytometry for analysis (events collected for analysis were $5\times10^4$). For T cells from spleen and lymph node analysis, the tissues were first mechanically disrupted and the cells were filtered through a 40 μm strainer for further analysis.

(9) Statistics.

All results presented are Mean±s. d. Statistical analysis was evaluated using GraphPad Prism (6.0). The log-rank test was performed for statistical analysis of survival time and two tailed Student's t-test was performed for other statistical analyses. With a P value <0.05, the differences between experimental groups and control groups were considered statistically significant.

D. REFERENCES

Advani, R. et al. Treatment of refractory and relapsed acute myelogenous leukemia with combination chemotherapy plus the multidrug resistance modulator PSC 833 (Valspodar). *Blood* 93, 787-795 (1999).

Brentjens, R. J. et al. CD19-targeted T cells rapidly induce molecular remissions in adults with chemotherapy-refractory acute lymphoblastic leukemia. *Sci. Transl. Med.* 5, 177ra138-177ra138 (2013).

Costinean, S. et al. Pre-B cell proliferation and lymphoblastic leukemia/high-grade lymphoma in Eμ-miR155 transgenic mice. *Proc. Natl Acad. Sci. USA* 103, 7024-7029 (2006).

Dick, J. E. Acute myeloid leukemia stem cells. *Ann. N. Y. Acad. Sci.* 1044, 1-5 (2005).

Ding, L. et al. Clonal evolution in relapsed acute myeloid leukemia revealed by whole genome sequencing. *Nature* 481, 506 (2012).

Döhner, H. et al. Diagnosis and management of acute myeloid leukemia in adults: recommendations from an international expert panel, on behalf of the European LeukemiaNet. *Blood* 115, 453-474 (2010).

Eeftens, J. M., van der Torre, J., Burnham, D. R. & Dekker, C. Copper-free click chemistry for attachment of biomolecules in magnetic tweezers. *BMC biophysics* 8, 9 (2015).

Ellebrecht, C. T. et al. Reengineering chimeric antigen receptor T cells for targeted therapy of autoimmune disease. *Science* 353, 179-184 (2016).

Estey, E. & Döhner, H. Acute myeloid leukaemia. *The Lancet* 368, 1894-1907 (2006).

Fernandez, H. F. et al. Anthracycline dose intensification in acute myeloid leukemia. *N. Engl. J. Med.* 361, 1249-1259 (2009).

Giralt, S. A. & Champlin, R. E. Leukemia relapse after allogeneic bone marrow transplantation: a review. *Blood* 84, 3603-3612 (1994).

Gottesman, M. M., Fojo, T. & Bates, S. E. Multidrug resistance in cancer: role of ATP-dependent transporters. *Nat. Rev. Cancer* 2, 48 (2002).

Hang, H. C., Yu, C., Kato, D. L. & Bertozzi, C. R. A metabolic labeling approach toward proteomic analysis of mucin-type O-linked glycosylation. *Proc. Natl Acad. Sci. USA* 100, 14846-14851 (2003).

Hu, C.-M. J. et al. Nanoparticle biointerfacing by platelet membrane cloaking. *Nature* 526, 118-121 (2015).

Hu, Q. et al. Engineered nanoplatelets for enhanced treatment of multiple myeloma and thrombus. *Adv. Mater.* 28, 9573-9580 (2016).

Huntly, B. J. & Gilliland, D. G. Leukaemia stem cells and the evolution of cancer-stem-cell research. *Nat. Rev. Cancer* 5, 311-321 (2005).

Ishida, Y., Agata, Y., Shibahara, K. & Honjo, T. Induced expression of PD-1, a novel member of the immunoglobulin gene superfamily, upon programmed cell death. *The EMBO journal* 11, 3887 (1992).

Jackson, H. J., Rafiq, S. & Brentjens, R. J. Driving CAR T-cells forward. *Nat. Rev. Clin. Oncol.* 13, 370-383 (2016).

Kamath, S., Blann, A. & Lip, G. Platelet activation: assessment and quantification. *Eur. Heart J.* 22, 1561-1571 (2001).

Keir, M. E. et al. Tissue expression of PD-L1 mediates peripheral T cell tolerance. *J. Exp. Med.* 203, 883-895 (2006).

Kershaw, M. H., Westwood, J. A. & Darcy, P. K. Gene-engineered T cells for cancer therapy. *Nat. Rev. Cancer* 13, 525-541 (2013).

Kingwell, K. CAR T therapies drive into new terrain. *Nat. Rev. Drug Discovery* 16, 301-304 (2017).

Lagasse, E. et al. Purified hematopoietic stem cells can differentiate into hepatocytes in vivo. *Nat. Med.* 6, 1229 (2000).

Leith, C. P. et al. Acute myeloid leukemia in the elderly: assessment of multidrug resistance (MDR1) and cytogenetics distinguishes biologic subgroups with remarkably distinct responses to standard chemotherapy. A Southwest Oncology Group study. *Blood* 89, 3323-3329 (1997).

Leith, C. P. et al. Frequency and clinical significance of the expression of the multidrug resistance proteins MDR1/P-glycoprotein, MRP1, and LRP in acute myeloid leukemia. A Southwest Oncology Group Study. *Blood* 94, 1086-1099 (1999).

Leopold, L. H. & Willemze, R. The treatment of acute myeloid leukemia in first relapse: a comprehensive review of the literature. *Leuk. Lymphoma* 43, 1715-1727 (2002).

Lowenberg, B., Downing, J. R. & Burnett, A. Acute myeloid leukemia. *N. Engl. J. Med.* 1999, 1051-1062 (1999).

Maude, S. L. et al. Chimeric antigen receptor T cells for sustained remissions in leukemia. *N. Engl. J. Med.* 371, 1507-1517 (2014).

McClanahan, F. et al. PD-L1 checkpoint blockade prevents immune dysfunction and leukemia development in a mouse model of chronic lymphocytic leukemia. *Blood* 126, 203-211 (2015).

Miyazaki, Y. et al. High shear stress can initiate both platelet aggregation and shedding of procoagulant containing microparticles. *Blood* 88, 3456-3464 (1996).

Moynihan, K. D. et al. Eradication of large established tumors in mice by combination immunotherapy that engages innate and adaptive immune responses. *Nat. Med.* 22, 1402-1410 (2016).

Ofran, Y. & Rowe, J. M. Treatment for relapsed acute myeloid leukemia: what is new? *Curr. Opin. Hematol.* 19, 89-94 (2012).

Pandolfi, A. et al. PAK1 is a therapeutic target in acute myeloid leukemia and myelodysplastic syndrome. *Blood* 126, 1118-1127 (2015).

Ruggeri, Z. M., Orje, J. N., Habermann, R., Federici, A. B. & Reininger, A. J. Activation-independent platelet adhesion and aggregation under elevated shear stress. *Blood* 108, 1903-1910 (2006).

Shi, P. et al. Spatiotemporal control of cell-cell reversible interactions using molecular engineering. *Nat. Commun.* 7 (2016).

Swami, A. et al. Engineered nanomedicine for myeloma and bone microenvironment targeting. *Proc. Natl Acad. Sci. USA* 111, 10287-10292 (2014).

Topalian, S. L. et al. Safety, activity, and immune correlates of anti-PD-1 antibody in cancer. *N. Engl. J. Med.* 366, 2443-2454 (2012).

Topalian, S. L., Drake, C. G. & Pardoll, D. M. Immune checkpoint blockade: a common denominator approach to cancer therapy. *Cancer Cell* 27, 450-461 (2015).

Tumeh, P. C. et al. PD-1 blockade induces responses by inhibiting adaptive immune resistance. *Nature* 515, 568 (2014).

Velez, J. et al. Platelets promote mitochondrial uncoupling and resistance to apoptosis in leukemia cells: a novel paradigm for the bone marrow microenvironment. *Cancer Microenviron.* 7, 79-90 (2014).

Wang, C. et al. In situ activation of platelets with checkpoint inhibitors for post-surgical cancer immunotherapy. *Nature Biomedical Engineering* 1, 0011 (2017).

Wilson, A. & Trumpp, A. Bone-marrow haematopoietic-stem-cell niches. *Nat. Rev. Immunol.* 6, 93-106 (2006).

Wu, C.-Y., Roybal, K. T., Puchner, E. M., Onuffer, J. & Lim, W. A. Remote control of therapeutic T cells through a small molecule-gated chimeric receptor. *Science* 350, aab4077 (2015).

Yan, M. & Jurasz, P. The role of platelets in the tumor microenvironment: From solid tumors to leukemia. *Biochim. Biophys. Acta* 1863, 392-400 (2016).

Yuan, H. et al. Multivalent bi-specific nanobioconjugate engager for targeted cancer immunotherapy. *Nat. Nanotechnol.* 12, 763-769 (2017).

Zhang, L., Gajewski, T. F. & Kline, J. PD-1/PD-L1 interactions inhibit antitumor immune responses in a murine acute myeloid leukemia model. *Blood* 114, 1545-1552 (2009).

Zhao, M. et al. Clickable Protein Nanocapsules for Targeted Delivery of Recombinant p53 Protein. *J. Am. Chem. Soc.* 136, 15319-15325 (2014).

Zhou, Q. et al. Depletion of endogenous tumor-associated regulatory T cells improves the efficacy of adoptive cytotoxic T-cell immunotherapy in murine acute myeloid leukemia. *Blood* 114, 3793-3802 (2009).

Zhou, Q. et al. Program death-1 signaling and regulatory T cells collaborate to resist the function of adoptively transferred cytotoxic T lymphocytes in advanced acute myeloid leukemia. *Blood* 116, 2484-2493 (2010).

What is claimed is:

1. A therapeutic agent delivery vehicle comprising a drug carrier and a targeting moiety, wherein the targeting moiety is treated with an activated azide molecule wherein the activated azide molecule comprises N-azidoacetylgalactosamine-tetraacylated (Ac4GalNAz), wherein the drug carrier is chemically conjugated to the targeting moiety via copper(I) catalyzed [3+2] azide-alkyne cycloaddition (CuAAC), strain-promoted azide-alkyne cycloaddition (SPAAC), or strain-promoted alkyne-nitrone cycloaddition (SPANC), wherein the drug carrier has been modified to comprise a therapeutic agent cargo wherein the therapeutic agent cargo comprises an immune checkpoint inhibitor, antibody, small molecule, peptide, polypeptide, polymer, peptide mimetic, nucleic acid, or drug combination.

2. The therapeutic agent delivery vehicle of claim 1, wherein the drug carrier is a modified platelet, synthetic microparticle, synthetic nanoparticle, or cell-derived vesicle.

3. The therapeutic agent delivery vehicle of claim 1, wherein the targeting moiety is a peptide, polypeptide, polymer, small molecule, nucleic acid, antibody, sugar, or cell.

4. The therapeutic agent delivery vehicle of claim 3, wherein the targeting moiety targets the bone marrow, liver, spleen, pancreas, prostate, bladder, heart, lung, brain, skin, kidneys, ovaries, testis, lymph nodes, small intestines, large intestines, or stomach.

5. The therapeutic agent delivery vehicle of claim 4, wherein the targeting moiety targets the bone marrow and the moiety is selected from the group consisting of hematopoietic stem cell, a peptide comprising repeats of Asp or Glu, or bone marrow targeting formulation.

6. The therapeutic agent delivery vehicle of claim 1, wherein the drug carrier has been modified to comprise a chemical linkage and/or the drug carrier is chemically conjugated to the targeting moiety.

7. The therapeutic agent delivery vehicle of claim 1, wherein the drug carrier is chemically conjugated to the targeting moiety via dibenzocyclooctyl (DBCO) copper-free cycloaddition.

8. The therapeutic agent delivery vehicle of claim 1, wherein the chemical linkage of the platelet comprises dibenzocyclooctyl (DBCO)-polyethylene glycol (PEG) 4 NHS ester.

9. The therapeutic agent delivery vehicle of claim 1, wherein the therapeutic agent cargo comprises an immune checkpoint inhibitor comprising a PD-1 inhibitor, a PD-L1 inhibitor, or CTLA-4 inhibitor.

10. The therapeutic agent delivery vehicle of claim 9, wherein the immune checkpoint inhibitor is attached to the surface of the modified platelet via a sulfosuccinimidyl-4-(N-maleimidomethyl)-cyclohexane-1-carboxylate (Sulfo-SMCC) linker.

11. A method of treating a cancer in a subject comprising administering to the subject the theraputic agent delivery vehicle of claim 1.

12. The method of treating cancer of claim 11, wherein the therapeutic agent delivery vehicle is administered to the patient at least once every 12, 14, 16, 18, 20, 22, 24, 26, 28, 30, 32, 34, 36, 38, 40, 42, 44, 46, 48 hours, once every 3, 4, 5, 6, 7, 8, 9, 10, 11, 12, 13, 14, 15, 16, 17, 18, 19, 20, 21, 22, 23, 24, 25, 26, 27, 28, 29, 30, 31 days, once every 2, 3, 4, 5, 6, 7, 8, 9, 10, 11, or 12 months.

13. The method of treating cancer of claim 11, further comprising administering a chemotherapeutic agent.

14. The method of treating a cancer of claim 11, wherein the cancer is selected from the group consisting of lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, renal cancer, small cell lung cancer and non-small cell lung cancer, neuroblastoma, glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, genitourinary cancer, pulmonary cancer, esophageal carcinoma, head and neck carcinoma, large bowel cancer, hematopoietic cancers; testicular cancer; colon cancers, and rectal cancers.

15. A method of treating a cancer in a subject comprising administering to the subject a therapeutic agent delivery vehicle of claim 1 comprising a modified platelet and a targeting moiety; wherein the modified platelet has been modified to comprise a therapeutic agent cargo and a chemical linkage; and wherein the modified platelet is chemically conjugated to the targeting moiety.

* * * * *

UNITED STATES PATENT AND TRADEMARK OFFICE
CERTIFICATE OF CORRECTION

PATENT NO. : 12,161,720 B2
APPLICATION NO. : 17/045586
DATED : December 10, 2024
INVENTOR(S) : Zhen Gu et al.

Page 1 of 1

It is certified that error appears in the above-identified patent and that said Letters Patent is hereby corrected as shown below:

In the Specification

In Column 1, Line 7, "62/653,843, filed on Apr. 6, 2019" should read --62/653,843, filed on Apr. 6, 2018--

In the Claims

In Column 40, Claim 11, Line 2, "the theraputic agent delivery" should read --the therapeutic agent delivery--

Signed and Sealed this
Eighth Day of April, 2025

Coke Morgan Stewart
*Acting Director of the United States Patent and Trademark Office*